United States Patent [19]

Latimer et al.

[11] Patent Number: 5,364,382
[45] Date of Patent: Nov. 15, 1994

[54] ABSORBENT STRUCTURE HAVING IMPROVED FLUID SURGE MANAGEMENT AND PRODUCT INCORPORATING SAME

[75] Inventors: Margaret G. Latimer, Roswell; Billie J. Matthews, Woodstock, both of Ga.; Ann M. Shershin, Kansas City, Mo.

[73] Assignee: Kimberly-Clark Corporation, Neenah, Wis.

[21] Appl. No.: 824,766

[22] Filed: Jan. 17, 1992

Related U.S. Application Data

[63] Continuation of Ser. No. 446,251, Dec. 5, 1989, abandoned, which is a continuation-in-part of Ser. No. 349,390, May 8, 1989, abandoned.

[51] Int. Cl.$^5$ .............................................. A61F 13/15
[52] U.S. Cl. .................................... 604/378; 604/358
[58] Field of Search ............... 604/378, 385.1, 385.2, 604/358

[56] References Cited

U.S. PATENT DOCUMENTS

| | | | |
|---|---|---|---|
| 2,761,449 | 9/1956 | Bletzinger | 128/285 |
| 3,016,599 | 1/1962 | Perry | 28/78 |
| 3,308,826 | 3/1967 | Blake | 128/290 |
| 3,369,544 | 2/1968 | Crockford | 128/285 |
| 3,523,536 | 8/1970 | Ruffo | 128/287 |
| 3,592,194 | 7/1971 | Duncan | 128/287 |
| 3,595,235 | 7/1971 | Jespersen | 128/284 |
| 3,612,055 | 10/1971 | Mesek et al. | 128/287 |
| 3,665,921 | 5/1972 | Stumpf | 128/287 |
| 3,666,348 | 5/1972 | Liloia et al. | 161/116 |
| 3,730,184 | 5/1973 | Mesek | 128/287 |
| 3,768,118 | 10/1973 | Ruffo et al. | 19/156.3 |
| 3,768,480 | 10/1973 | Mesek et al. | 128/287 |
| 3,772,417 | 11/1973 | Vogt | 264/230 |
| 3,777,758 | 12/1973 | Mesek et al. | 128/284 |
| 3,806,289 | 4/1974 | Schwarz | 425/72 |
| 3,837,343 | 9/1974 | Mesek | 128/287 |
| 3,871,378 | 3/1975 | Duncan et al. | 128/290 |
| 3,908,659 | 9/1975 | Wehrmeyer | 128/287 |
| 3,927,673 | 12/1975 | Taylor | 128/287 |
| 3,945,386 | 3/1976 | Anczurowski | 128/287 |

(List continued on next page.)

FOREIGN PATENT DOCUMENTS

| | | |
|---|---|---|
| 0108637 | 5/1984 | European Pat. Off. . |
| 0165807 | 12/1985 | European Pat. Off. . |
| 0174775 | 3/1986 | European Pat. Off. . |
| 0193309 | 9/1986 | European Pat. Off. . |
| 0254476 | 1/1988 | European Pat. Off. . |
| 0317058 | 5/1989 | European Pat. Off. . |
| 03525379 | 1/1987 | Germany . |
| 61-2854 | 1/1986 | Japan . |
| 01308935 | 3/1973 | United Kingdom . |
| 01389891 | 4/1975 | United Kingdom . |
| 1402327 | 8/1975 | United Kingdom . |
| 01547524 | 6/1979 | United Kingdom . |
| 2023068 | 12/1979 | United Kingdom . |
| 2055586 | 3/1981 | United Kingdom . |
| 2063683 | 6/1981 | United Kingdom . |
| 2087240 | 5/1982 | United Kingdom . |
| 2089214 | 6/1982 | United Kingdom . |
| 2101038 | 1/1983 | United Kingdom . |
| 2101338 | 1/1983 | United Kingdom . |
| 2131699 | 6/1984 | United Kingdom . |
| 2145661 | 4/1985 | United Kingdom . |
| 2170108 | 7/1986 | United Kingdom . |
| 2214201A | 8/1989 | United Kingdom . |
| WO80/01455 | 7/1980 | WIPO . |
| WO86/05661 | 9/1986 | WIPO . |

*Primary Examiner*—Randall L. Green
*Assistant Examiner*—Rob Clarke
*Attorney, Agent, or Firm*—Paul Yee

[57] ABSTRACT

An absorbent article includes a retention portion for storing absorbed liquids, and a distinctive surge management portion. The surge management portion, which has a selected basis weight, is constructed to rapidly uptake and temporarily hold at least three (3) successive surges of liquid directed into the target zone of the article and then release each of the surges to the retention portion. The retention portion desorbs each input of liquid from the surge management portion and stores the liquid. Particular functional and structural parameters can further characterize the surge management portion of the absorbent article.

81 Claims, 10 Drawing Sheets

U.S. PATENT DOCUMENTS

| | | | |
|---|---|---|---|
| 3,952,124 | 4/1976 | Mesek | 128/287 |
| 3,965,905 | 6/1976 | Schoenholz et al. | 128/285 |
| 3,965,906 | 6/1976 | Karami | 128/287 |
| 3,978,185 | 8/1976 | Buntin et al. | 264/93 |
| 3,987,792 | 10/1976 | Hernandez | 128/284 |
| 4,014,341 | 3/1977 | Karami | 128/287 |
| 4,018,862 | 4/1977 | Saito | 264/137 |
| 4,041,951 | 8/1977 | Sanford | 128/287 |
| 4,044,768 | 8/1977 | Mesek et al. | 128/287 |
| 4,045,833 | 9/1977 | Mesek et al. | 5/335 |
| 4,077,410 | 3/1978 | Butterworth et al. | 128/287 |
| 4,103,058 | 7/1978 | Humlicek | 428/171 |
| 4,118,531 | 10/1978 | Hauser | 428/224 |
| 4,212,302 | 7/1980 | Karami | 128/287 |
| 4,216,772 | 8/1980 | Tsuchiya et al. | 128/284 |
| 4,223,677 | 9/1980 | Anderson | 128/287 |
| 4,232,674 | 11/1980 | Melican | 128/287 |
| 4,238,175 | 12/1980 | Fujii et al. | 425/83.1 |
| 4,259,958 | 4/1981 | Goodbar | 128/287 |
| 4,285,342 | 8/1981 | Mesek | 128/287 |
| 4,304,234 | 8/1981 | Hartmann | 128/287 |
| 4,324,247 | 4/1982 | Aziz | 128/287 |
| 4,338,371 | 7/1982 | Dawn et al. | 428/283 |
| 4,364,992 | 12/1982 | Ito et al. | 428/283 |
| 4,372,312 | 2/1983 | Fendler et al. | 128/290 |
| 4,374,888 | 2/1983 | Bornslaeger | 428/198 |
| 4,381,611 | 5/1983 | Wishman | 34/9 |
| 4,381,782 | 5/1983 | Mazurak et al. | 604/368 |
| 4,392,861 | 7/1983 | Butterworth et al. | 604/366 |
| 4,392,862 | 7/1983 | Marsan et al. | 604/366 |
| 4,397,644 | 8/1983 | Matthews et al. | 604/378 |
| 4,405,325 | 9/1983 | Antifinger et al. | 604/370 |
| 4,413,032 | 11/1983 | Hartmann et al. | 428/288 |
| 4,414,647 | 12/1983 | Shipp, Jr. et al. | 428/212 |
| 4,421,813 | 12/1983 | Athey | 428/195 |
| 4,436,780 | 3/1984 | Hotchkiss et al. | 428/198 |
| 4,461,621 | 7/1984 | Karami et al. | 604/368 |
| 4,468,428 | 8/1984 | Early et al. | 428/221 |
| 4,480,000 | 10/1984 | Watanabe et al. | 428/284 |
| 4,496,358 | 1/1985 | Karami et al. | 604/379 |
| 4,500,315 | 2/1985 | Pieniak et al. | 604/379 |
| 4,501,586 | 2/1985 | Holtman | 604/380 |
| 4,519,798 | 5/1985 | Dinius | 604/358 |
| 4,519,799 | 5/1985 | Sakurai | 604/366 |
| 4,531,945 | 7/1985 | Allison | 604/378 |
| 4,535,020 | 8/1985 | Thomas et al. | 428/131 |
| 4,537,590 | 8/1985 | Pieniak et al. | 604/379 |
| 4,540,414 | 9/1985 | Wishman | 604/378 |
| 4,540,454 | 9/1985 | Pieniak et al. | 156/62.2 |
| 4,550,725 | 11/1985 | Wishman | 128/155 |
| 4,551,143 | 11/1985 | Cook et al. | 604/371 |
| 4,559,051 | 12/1985 | Hanson | 604/385 |
| 4,560,372 | 12/1985 | Pieniak | 604/369 |
| 4,573,988 | 3/1986 | Pieniak et al. | 604/379 |
| 4,578,066 | 3/1986 | O'Connor | 604/366 |
| 4,578,070 | 3/1986 | Holtman | 604/378 |
| 4,578,414 | 3/1986 | Sawyer et al. | 524/310 |
| 4,590,114 | 5/1986 | Holtman | 428/171 |
| 4,608,292 | 8/1986 | Lassen | 428/131 |
| 4,623,340 | 11/1986 | Luceri | 604/385 |
| 4,623,576 | 11/1986 | Lloyd et al. | 428/171 |
| 4,636,209 | 1/1987 | Lassen | 604/378 |
| 4,654,040 | 3/1987 | Luceri | 604/385 |
| 4,655,757 | 4/1987 | McFarland et al. | 604/366 |
| 4,673,402 | 6/1987 | Weisman et al. | 604/368 |
| 4,675,013 | 6/1987 | Ruffo | 604/366 |
| 4,681,577 | 7/1987 | Stern et al. | 604/378 |
| 4,699,619 | 10/1987 | Bernardin | 604/378 |
| 4,699,620 | 10/1987 | Bernardin | 604/385 |
| 4,704,112 | 11/1987 | Suzuki et al. | 604/378 |
| 4,707,398 | 11/1987 | Boggs | 428/224 |
| 4,735,624 | 4/1988 | Mazars | 604/378 |
| 4,738,676 | 4/1988 | Osborn, III | 604/385 |
| 4,755,178 | 7/1988 | Insley et al. | 604/367 |
| 4,755,179 | 7/1988 | Shiba et al. | 604/370 |
| 4,794,034 | 12/1988 | Nishizawa et al. | 428/218 |
| 4,798,603 | 1/1989 | Meyer et al. | 604/378 |
| 4,923,454 | 5/1990 | Seymour et al. | 604/368 |
| 4,988,344 | 1/1991 | Reising et al. | 604/368 |
| 4,988,345 | 1/1991 | Reising | 524/310 |
| 5,135,521 | 8/1992 | Luceri et al. | 604/383 |

ABSORBENT STRUCTURE HAVING IMPROVED FLUID SURGE MANAGEMENT AND PRODUCT INCORPORATING SAME

This is a continuation of copending U.S. application Ser. No. 07/446,251 filed on Dec. 5, 1989, now abandoned; which in turn is a continuation-in-part of copending U.S. application Ser. No. 07/349,390 filed May 8, 1989, now abandoned.

TECHNICAL FIELD

This invention relates to absorbent articles, particularly absorbent structures which are useful in personal care products. More particularly, the invention relates to absorbent articles which have a portion designed for rapid uptake, and subsequent release of repeated liquid surges to the remainder of the article.

BACKGROUND OF THE INVENTION

Desired performance objectives of personal care absorbent products include low leakage from the product and a dry feel to the wearer. However, absorbent products commonly fail before the total absorbent capacity of the product is utilized. An absorbent garment, for example a disposable diaper, often leaks at the leg, top front or top back areas of the diaper. Leakage can occur due to a variety of shortcomings in the product, one being an insufficient rate of fluid uptake by the absorbent system, especially on the second, third or fourth liquid surges.

It has been found that micturition can occur at rates as high as 15 to 20 milliliters per second and at velocities as high as 280 centimeters per second. Conventional diaper absorbent structures, such as those comprising admixtures of absorbent gelling particles and cellulosic fluffed pulp, may initially uptake fluid at rates of only about 8 milliliters per second or less, depending somewhat on the web density and concentration of gelling particulates. Even the rates for these fabrics can deteriorate once they have already received liquid surges into their structures. The above disparity between liquid delivery and uptake rates can result in excessive pooling on the surface of the fabric before it is taken up by the structure. In the meantime, pooled fluid can leak from the leg opening of the diaper and soil the outer clothing or bedding of the wearer.

Attempts to alleviate leakage include providing physical barriers with elastic leg gathers and changing the amount or configuration of the absorbent material at the zone of the structure into which the liquid surges typically occur. Absorbent gelling particles have also been included to increase the liquid holding capacity in various regions of the absorbent structure.

Absorbent articles have typically employed various types of absorbent pads composed of cellulosic fibers. For example, U.S. Pat. No. 3,523,536 to Ruffo discloses an absorbent fibrous web of predominantly shorter fibers intermixed with relatively longer fibers for purposes of stabilizing the web. U.S. Pat. No. 3,768,118 to Ruffo, et al. relates to a process for blending longer and shorter fibers. U.S. Pat. No. 3,663,348 to Liloia, et al. discloses an absorbent product in which a disclosed fabric serves as a body side, fluid pervious liner material, and an absorbent core includes a loosely compacted cellulose batt with a densified layer on one side.

Particular absorbent garments have been configured to control the distribution of absorbed liquids. U.S. Pat. No. 4,578,070 to Holtman discloses incontinence pads which include a bilayer, corrugated nonwoven structure. U.S. Pat. No. 4,681,577 to Stern and Holtman discloses incontinence pads placed in a liquid-impermeable, flexible shell. The absorbent structure disclosed in the '577 patent includes either a corrugated or uncorrugated version of the bilayer nonwoven structure disclosed in the '070 patent, located in the front portion of the product. A second resilient, open structure, such as a resilient nonwoven or open cell foam, in the back portion is further disclosed for the purpose of providing fecal waste containment.

U.S. Pat. No. 4,699,619 to Bernardin discloses another cellulosic absorbent structure which can comprise a multi-layer core arrangement wherein a top layer has a greater pore size than that of an underlying layer. The pore size gradient between the core layers can be achieved in various ways, for example, by using webs of different densities or webs with a common density but formed from fibers of different sizes. A portion of superabsorbent material can also be placed at various locations within the absorbent structure.

European Application No. 254,476 of Alemany et al. discloses an absorbent member having fluid storage and acquisition zones composed of cellulosic fluff mixed with absorbent gelling particles. The particles are purportedly used to keep the fibrous structure from collapsing when wet. The acquisition zone has a lower density and lower basis weight than that of the storage zone. U.S. Pat. No. 4,673,402 to Weisman, et al. discloses a dual-layer absorbent core arrangement comprising a bottom fluff pad containing hydrogel particles, and a top fluff pad with little or no hydrogel particles.

Non-woven materials such as carded webs and spunbonded webs, have been used as the body-side liners in absorbent products. Specifically, very open, porous liner structures have been employed to allow liquid to pass through them rapidly, and help keep the body skin separated from the wetted absorbent pad underneath the liner. In addition other layers of material, such as those constructed with thick, lofty fabric structures, have been interposed between the liner and absorbent pad for the purpose of reducing wet-back.

With conventional fluff-based absorbent structures, such as those discussed above, the cellulosic fibers, when wetted, can lose resiliency and collapse. As a result, the liquid uptake rate of the wetted structures may become too low to adequately accommodate subsequent, successive liquid surges. Where absorbent gelling particles are incorporated between the fibers to hold them apart, the gelling particles swell and do not release the absorbed fluid. Swelling of the particles can then diminish the void volume of the absorbent structure and reduce the ability of the structure to rapidly uptake liquid.

The addition of more absorbent material, e.g., secondary fluff pledgets, or absorbent gelling particles has been employed to increase holding capacity. The desired rate of liquid intake within such arrangements, however, may not be sufficiently sustained during successive liquid surges.

Despite the development of absorbent structures of the types surveyed above, there remains a need for improved absorbent structures which can adequately reduce the incidence of leakage from absorbent products, such as disposable diapers. There is a need for an absorbent structure which can provide improved handling of liquid surges and more effectively uptake and retain repeated loadings of liquid during use.

SUMMARY OF THE INVENTION

An absorbent article for absorbing and containing body fluids, comprises a surge management portion for rapidly uptaking liquid, and a retention portion which receives and retains liquid released from the surge management portion. The surge management portion comprises a fibrous material which has a basis weight of at least about 60 grams per square meter, and is constructed to provide for an intake time value of not more than about 12 seconds, a temporary loading value capacity of at least about 3 gm per gram of surge management material, and a residual value, after desorption, of no more than about 1 gm per gram of surge management material. The surge management portion is constructed to provide the desired intake time value, temporary loading value and residual value for at least three successive cycles of liquid uptake and desorption.

The absorbent structure of the present invention advantageously provides a surge management portion which can rapidly uptake body exudates and can maintain the rate of uptake even after the absorbent structure has been previously wetted with one or more liquid insults. The invention can also provide a transitional, limited-time reservoir for temporarily containing each liquid surge occurring in the target zone of the absorbent structure, and can further provide a more complete release and movement of the liquid into the retention portion of the structure. As a result, a garment which includes the distinctive absorbent structure of the present invention can help avoid puddling of liquid against the wearer's skin, and more rapidly move the liquid away from the skin and into the absorbent structure. The transitional reservoir function of the invention can advantageously allow the retention portion a greater period of time in which to accept repeated surges of liquid while also isolating the liquid away from the wearer's skin. The more complete release of the liquid into the retention portion helps to maintain a dryer section of the garment against the wearer. Thus, the distinctive structure of the present invention can reduce the amount of liquid held against the wearer's skin, reduce leakage of liquid from the absorbent structure, and provide improved dryness and comfort to the wearer. In addition, the distinctive aspects of the present invention can be advantageously sustained during the course of multiple insults of liquid delivered into the absorbent structure.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The absorbent structures of the present invention will be described herein in relationship to their use in disposable absorbent articles, but it should be understood that potential uses of the absorbent structures of the present invention need not be limited to disposable absorbent articles. As used herein, the term "disposable absorbent article" refers to articles which absorb and contain body exudates and are intended to be discarded after a limited period of use (i.e., they are not intended to be laundered or otherwise restored for reuse). The articles can be placed against or in proximity to the body of the wearer to absorb and contain various exudates discharged from the body. While the present description will particularly be made in the context of a diaper article, it should be understood that the present invention is also applicable to other disposable personal care absorbent articles, such as incontinence garments, sanitary napkins, and the like, as well as surgical bandages and sponges.

Figure 1:
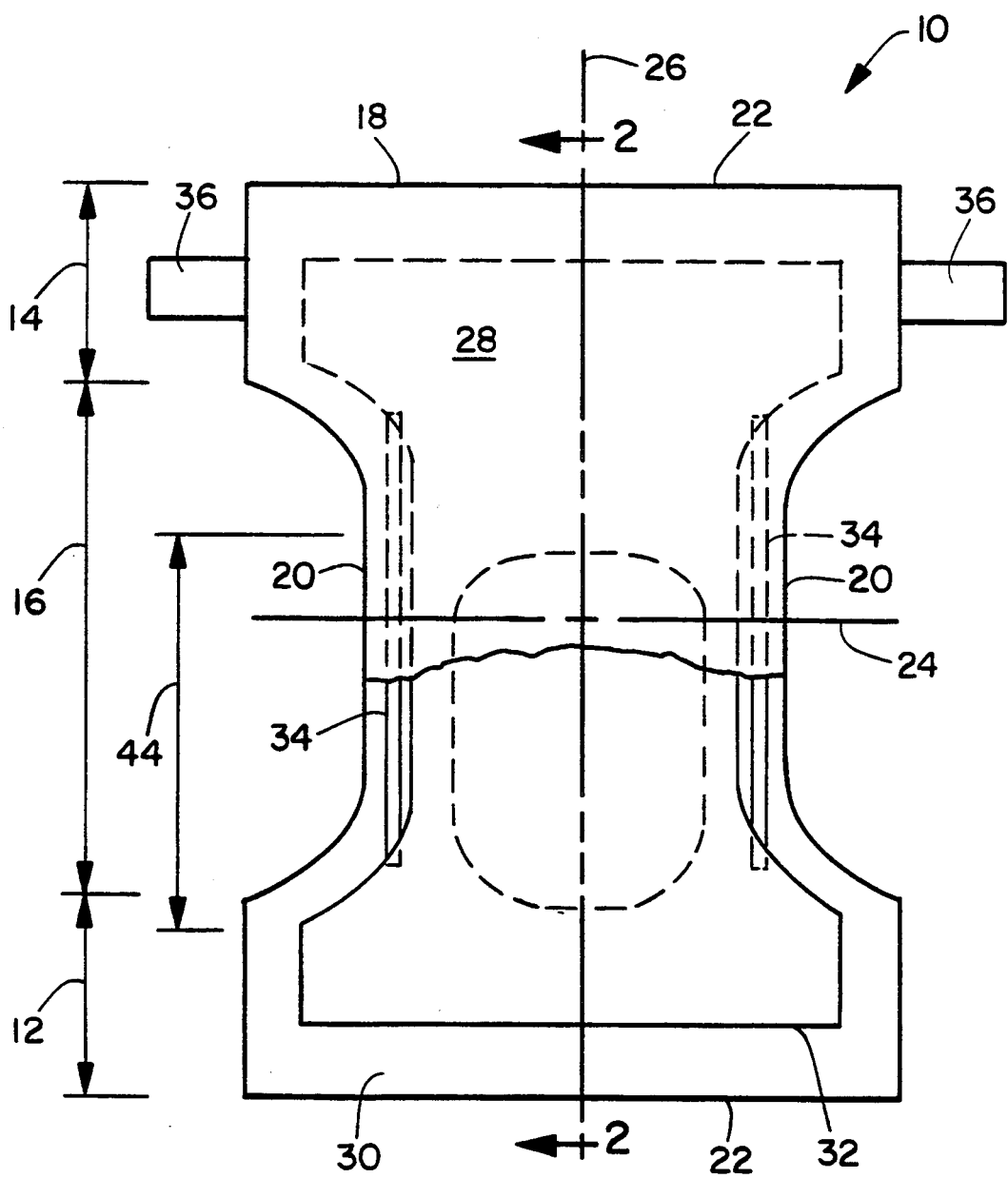
FIG. 1 is a plan view showing a disposable diaper embodiment of the present invention wherein a portion of the top sheet has been cut away to more clearly show the underlying absorbent structure of the diaper.
Figure 2:
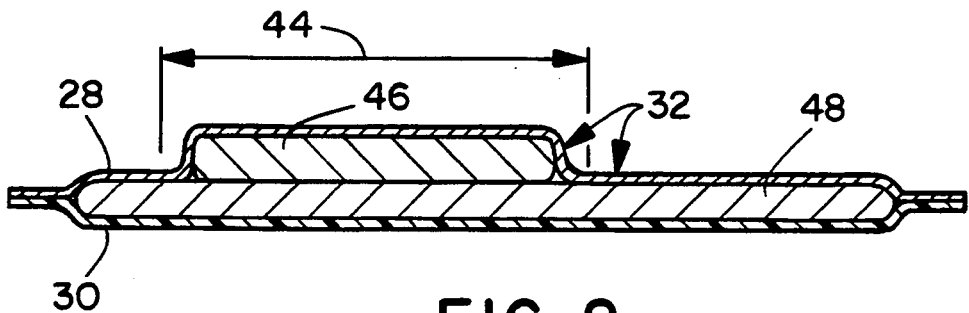
FIG. 2 is a longitudinal sectional view taken along sectional lines 2—2 of FIG. 1.

Referring to FIGS. 1 and 2, an absorbent article, such as diaper 10, includes a retention means, such as retention portion 48, which is configured to contain and hold a selected liquid. The article also includes a surge management means, such as surge management portion 46, which is located in liquid communication with retention portion 48. The surge management portion receives liquid and subsequently releases the liquid to the retention means. Surge management portion 46 is composed of a fibrous material and has a basis weight of at least about 60 gsm. The surge management portion is constructed and arranged to provide for an uptake time value of not more than 12 seconds, a liquid residual value of not more than about 1 gm per gram of the surge management portion, and a temporary loading value of at least about 3 gm of liquid per gram of the surge management portion.

In a particular aspect of the invention, the uptake time value is not more than about 10 sec, and preferably is not more than about 8 sec to provide improved performance. In another aspect of the invention, the temporary loading value is at least about 6 gm/gram of fabric, and preferably is at least about 9 gm/gram of fabric to provide improved effectiveness. In yet another aspect of the invention, the residual value is not more than about 0.75 gm/gram of fabric, and preferably is not more than about 0.5 gm/gram of fabric to provide further improvements.

In still other aspects of the invention, the surge management portion can be characterized by various distinctive structural parameters. The parameters include, for example, the wet resiliency value, the total fiber-surface-area, the wettable fiber-surface-area, the nonwettable fiber-surface-area, and the density of the surge management material.

FIG. 1 is a representative plan view of the diaper 10 of the present invention in its flat-out, uncontracted state (i.e., with all elastic induced gathering and contraction removed) with portions of the structure being partially cut away to more clearly show the construction of the diaper 10, and with the portion of the diaper 10 which contacts the wearer facing the viewer. The diaper 10 is shown in FIG. 1 to have a front waistband region 12, a back waistband region 14, a crotch region 16, and a periphery 18 which is defined by the outer edges of the diaper in which the longitudinal edges are designated 20 and the end edges are designated 22. The diaper additionally has a transverse center line 24 and a longitudinal center line 26.

The diaper 10 comprises a liquid permeable top sheet 28; a substantially liquid impermeable back sheet 30; an absorbent structure generally shown at 32 positioned between the top sheet and backsheet; and elastic members 34. Topsheet 28, backsheet 30, absorbent structure 32, and the elastic members 34 may be assembled in a variety of well-known diaper configurations. It should be recognized, however, that in articles other than diapers, individual components, such as top sheet 28, back sheet 30 and elastic members 34, may be optional. The desirability of including particular components in other absorbent articles would depend upon their intended end use.

In the shown embodiment of diaper 10, top sheet 28 and the backsheet 30 are coextensive and have length and width dimensions generally larger than those of the absorbent structure 32. The top sheet 28 is associated with and superimposed on the back sheet 30, thereby defining the periphery 18 of the diaper 10. The periphery delimits the outer perimeter or the edges of the diaper 10, and comprises end edges 22 and longitudinal edges 20. The diaper 10 has front and back waistband regions 12 and 14, respectively extending from the end edges 22 of the diaper periphery 18 toward the transverse center line 24 of the diaper a distance from about 2 percent to about 10 percent and preferably about 5 percent of the length of the diaper 10. The waistband regions comprise those upper portions of the diaper 10, which when worn, wholly or partially cover or encircle the waist or mid-lower torso of the wearer. The intermediate, crotch region 16 lies between and interconnects waistband regions 12 and 14, and comprises that portion of the diaper 10 which, when worn, is positioned between the legs of the wearer and covers the lower torso of the wearer. Thus, the crotch region 16 is the area where repeated fluid surge typically occur in the diaper 10 or other disposable absorbent article.

The top sheet 28, if employed, presents a body-facing surface which is compliant, soft-feeling, and non-irritating to the wearer's skin. Further, the top sheet 28 is sufficiently porous to be liquid permeable, permitting liquid to readily penetrate through its thickness. A suitable top sheet 28 may be manufactured from a wide range of web materials, such as porous foams, reticulated foams, apertured plastic films, natural fibers (for example, wood or cotton fibers), synthetic fibers (for example, polyester or polypropylene fibers), or a combination of natural and synthetic fibers. The top sheet 28 is typically employed to help isolate the wearer's skin from liquids held in the absorbent structure 32.

Various woven and nonwoven fabrics can be used for the top sheet 28. For example, the topsheet may be composed of a meltblown or spunbonded web of polyolefin fibers. The topsheet may also be a bonded-carded-web composed of natural and synthetic fibers. The term "nonwoven web" means a web of material which is formed without the aid of a textile weaving or knitting process. The term "fabrics" is used to refer to all of the woven, knitted and nonwoven fibrous webs.

The back sheet 30 is substantially impermeable to liquids and is typically manufactured from a thin plastic film, or other flexible liquid-impermeable material. As used in the present specification, the term "flexible" refers to materials which are compliant and which will readily conform to the general shape and contours of the wearer's body. The back sheet 30 prevents the exudates contained in the absorbent structure 32 from wetting articles such as bedsheets and overgarments which contact the diaper 10. In the shown embodiment, the back sheet 30 is a polyethylene film having a thickness of from about 0.012 millimeters (0.5 mil) to 0.051 millimeters (2.0 mils). Alternatively, the back sheet may be a woven or nonwoven fibrous web layer which has been constructed or treated to impart the desired level of liquid impermeability.

Back sheet 30 may optionally be composed of a "breathable" material which permits vapors to escape from the absorbent structure 32 while still preventing liquid exudates from passing through the back sheet. The back sheet can also be embossed and/or matte finished to provide a more aesthetically pleasing appearance.

The size of the back sheet 30 is determined by the size of the absorbent structure 32 and the exact diaper design selected. The back sheet 30, for example, may have a generally T-shape, a generally I-shape or a modified hourglass shape, and may extend beyond the terminal edges of absorbent structure 32 by a selected distance, e.g., 1.3 centimeters to 2.5 centimeters (0.5 to 1.0 inch).

The top sheet 28 and the back sheet 30 are connected or otherwise associated together in an operable manner. As used therein, the term "associated" encompasses configuration of the top sheet 28 is directly joined to the back sheet 30 by affixing the top sheet 28 directly to the back sheet 30, and configurations whereby the top sheet 28 is then directly joined to the back sheet 30 by affixing the top sheet 28 to intermediate members which in turn are affixed to the back sheet 30. The top sheet 28 and the back sheet 30 can be affixed directly to each other in the diaper periphery 18 by attachment means (not shown) such as an adhesive, sonic bonds, thermal bonds or any other attachment means known in the art. For example, a uniform continuous layer of adhesive, a patterned layer of adhesive, or an array of separate lines or spots of construction adhesive may be used to affix the top sheet 28 to the back sheet 30.

Fastening means, such as tape tab fasteners 36, are typically applied to the back waistband region 14 of the diaper 10 to provide a mechanism for holding the diaper on the wearer. The tape tab fasteners 36 can be any of those well known in the art, and are typically applied to the corners of the diaper 10. For example, mechanical fasteners, hook and loop fasteners, snaps, pins or buckles, may be used rather than, or in combination with adhesives and other means. It should be understood that is may be possible to dispense with the fasteners in a given design configuration.

The elastic members 34, if included in the particular article, are disposed adjacent the periphery 18 of the diaper 10, preferably along each longitudinal edge 20 so that the elastic members 34 tend to draw and hold the diaper 10 against the legs of the wearer. Elastic members 34 may also be disposed adjacent either or both of the end edges 22 of the diaper 10 to provide an elasticized waistband. It should be noted that elasticized leg gathers and waist gathers are typically used in conventional diapers to reduce leakage caused by inadequacies of conventional absorbent structures and materials. In some instances the present invention may be advantageously configured to lessen reliance on the elasticized gathers for liquid containment purposes.

The elastic members 34 are secured to the diaper 10 in an elastically contractible condition so that in a normal under strain configuration, the elastic members effectively contract against the diaper 10. The elastic members 34 can be secured in an elastically contractible condition in at least two ways, for example, the elastic members 34 may be stretched and secured while the diaper 10 is in an uncontracted condition. Alternatively, the diaper 10 may be contracted, for example, by pleating, and the elastic members 34 secured and connected to the diaper 10 while the elastic members 34 are in their unrelaxed or unstretched condition. Still other means, such as heat-shrink elastic material, may be used to gather the garment.

In the embodiment illustrated in FIG. 1, the elastic members 34 extend essentially the length of the crotch region 16 of the diaper 10. Alternatively, the elastic members 34 may extend the entire length of the diaper 10, or any other length suitable providing the arrangement of elastically contractible lines desired for the particular diaper design.

The elastic members 34 may have any of a multitude of configurations. For example, the width of the individual elastic members 34 may be varied from 0.25 millimeters (0.01 inches) to 25 millimeters (1.0 inches) or more; the elastic members 34 may comprise a single strand of elastic material or may comprise several parallel or non-parallel strands of elastic material; or may be applied in a rectilinear or curvilinear arrangement. The elastic members 34 may be affixed to the diaper in any of several ways which are known in the art. For example, the elastic members 34 may be ultrasonically bonded, heat and pressure sealed using a variety of bonding patterns or adhesively bonded to the diaper 10.

The absorbent structure 32 is positioned between the top sheet 28 and the back sheet 30 to form the diaper 10. The absorbent structure is generally compressible, conformable, non-irritating to the wearer's skin, and capable of absorbing and retaining liquid body exudates. Referring to FIGS. 2-6, it should be understood that, for purposes of this invention, the absorbent structure could comprise a single, integral piece of material, or alternatively could comprise a plurality of individual separate pieces of material. Where the absorbent structure comprises a single, integral piece of material, the material could include selected structural features formed in different regions thereof. Where the absorbent structure comprises multiple pieces, the pieces may be configured as layers or other nonplanar shapes. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

Figure 3:
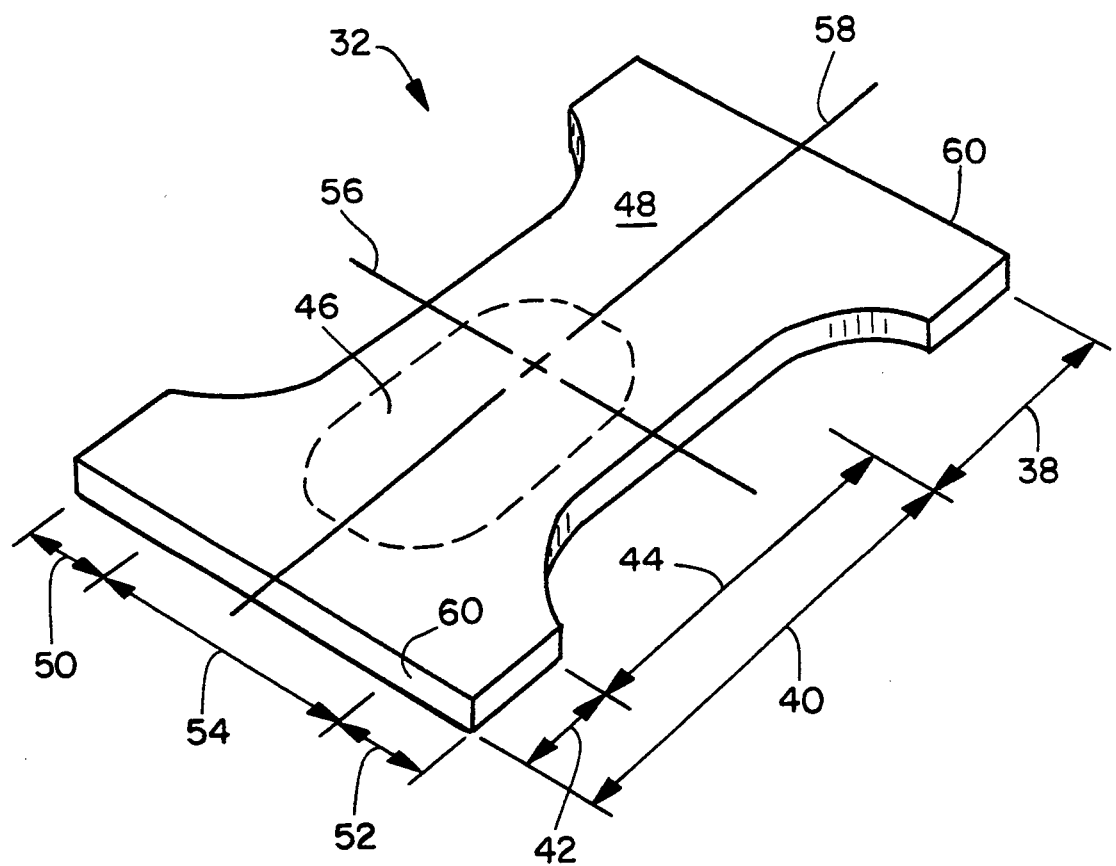
FIG. 3 is a perspective view of an absorbent structure of the present invention.
Figure 5:
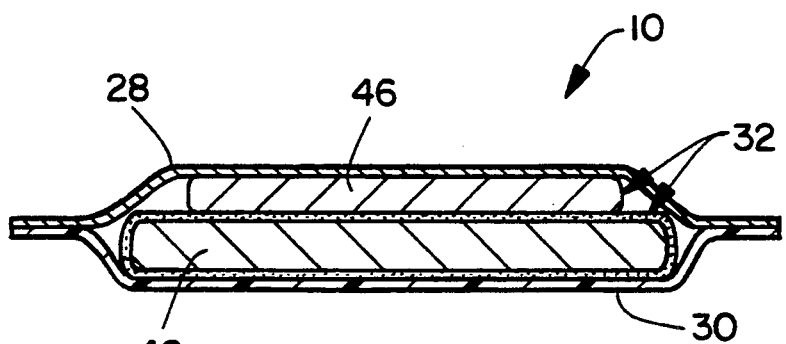
FIG. 5 is a cross-sectional view of FIG. 4, taken along sectional lines 5—5.
Figure 6:
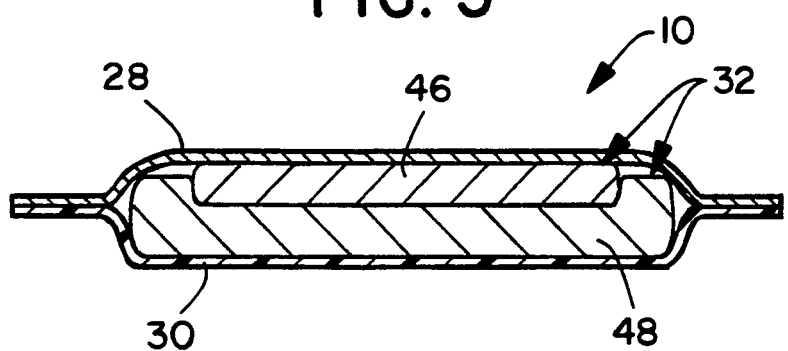
FIG. 6 is a cross-sectional view of an alternate embodiment of the dual-layer core of the diaper of the present invention of FIG. 4.

In the embodiment representatively shown in FIG. 3, absorbent structure 32 includes a back section 38 and a front section 40, and the front section has an end region 42 and a target zone 44. The absorbent article generally comprises a liquid surge management portion 46 (shown by the dotted lines), and a liquid retention portion 48 arranged in liquid communication with surge management portion 46. The absorbent structure additionally has a transverse center line 56 and a longitudinal center line 58. At least a part of surge management portion 46 is located within target zone 44, and preferably, the surge management portion has an areal extent which extends completely over target zone 44. Retention portion 48 is positioned in liquid communication with surge management portion 46 to receive liquids released from the surge management portion, and to hold and store the liquid. The absorbent structure may be configured with a part of retention portion 48 located within target zone 44 and the remainder of retention portion 48 located outside of the target zone. In an alternative arrangement, none of the retention portion is positioned within target zone 44, and the retention portion is totally located outside of the target zone. In yet another arrangement, all of retention portion 48 may be positioned within target zone 44. The retention portion can include a recess area which wholly or partially surrounds surge management portion 46 (FIG. 6), or can be entirely positioned below the surge management portion (FIG. 5). The arrangement which includes the recess in retention portion 48 can advantageously increase the area of contact and liquid communication between the retention portion and surge management portion 48.

Front section 40 is conceptually divided into three regions comprising two transversely spaced ear regions 50 and 52 respectively, and a central region 54. Front section 40 is contiguous with back section 38, and the back and front sections of absorbent structure 32 extend away from the end edges 60 of the absorbent structure 32 toward the transverse center line 56. The relative dimensions of the various sections and portions of the diaper 10, and of the absorbent structure 32, can be varied depending on materials used and the desired product needs. For example, the front portion 40 can extend over a distance corresponding to about one-half to two-thirds, or even three-fourths of the length of absorbent structure 32. The front section 40 is constructed to encompass all the fluid target zone 44 of the absorbent structure 32 within the diaper or other absorbent article.

The front portion 40 has an end region 42 and a target zone 44. The end region 42 comprises the portion of the front section 40 extending a selected distance from the respective end edge 60 of the absorbent structure 32 toward the transverse center line 56. The target zone 44 is contiguous with end region 42 and back section 38, and encompasses the area where repeated liquid surges typically occur in absorbent structure 32. The particular location where liquid is discharged, such as during micturition, varies depending on the age and gender of the wearer. For example, male infants tend to urinate further toward the front end of the diaper. The female target zone is located closer to the center of the crotch. As a result, the shape and relative longitudinal placement of the surge management portion 46 can be selected to best correspond with the actual target zone of either or both categories of wearers.

The ear regions 50 and 52 comprise portions which generally extend from the longitudinal edges 20 (FIG. 1) of the periphery 18 toward the longitudinal center line a distance from one-tenth to one-third of the overall width of the absorbent structure 32, and connect to central region 54. Thus, the ear regions are configured to engage the sides of the wearer's waist and torso, and the central region 54 is configured to engage the medial portion of the wearer's waist and torso.

The absorbent structure 32 may be manufactured in a wide variety of sizes and shapes (for example, rectangular, trapezoidal, T-shape, I-shape, hourglass shape, etc.) and from a wide variety of materials. The size and the absorbent capacity of the absorbent structure 32 should be compatible with the size of the intended wearer and the liquid loading imparted by the intended use of the absorbent article. Further, the size and the absorbent capacity of the absorbent structure 32 can be varied to accommodate wearers ranging from infants through adults. In addition, it has been found that with the present invention, the densities and/or basis weights of the respective surge management 46 and retention 48 portions, as well as their relative ratios, can be varied.

Various types of wettable, hydrophilic fibrous material can be used in the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fibers or blends of fibers used for the surge management portion 46 can be provided by a Cahn SFA-222 Surface Force Analyzer System. When measured with this system in accordance with the procedure described in detail herein below, fibers having contact angles less than 90° are designated "wettable", while fibers having contact angles greater than 90° are designated "nonwettable".

A capillary force differential created at the interface between the surge management 46 and retention 48 portions can improve the containment characteristics of the absorbent structure 32. If surge management portion 46 has and maintains a relatively lower capillary attraction, as compared to the capillary attraction exhibited by retention portion 48, liquid surges occurring in the target zone 44 tend to be desorbed more readily from the surge management portion and into the retention portion. Because the retention portion 48 can thereby have a relatively higher capillarity than the surge management portion 46, the liquid surges tend to be drawn into the retention portion 48 and distributed to the more remote regions thereof by wicking along the plane generally defined by the retention portion.

Figure 4:
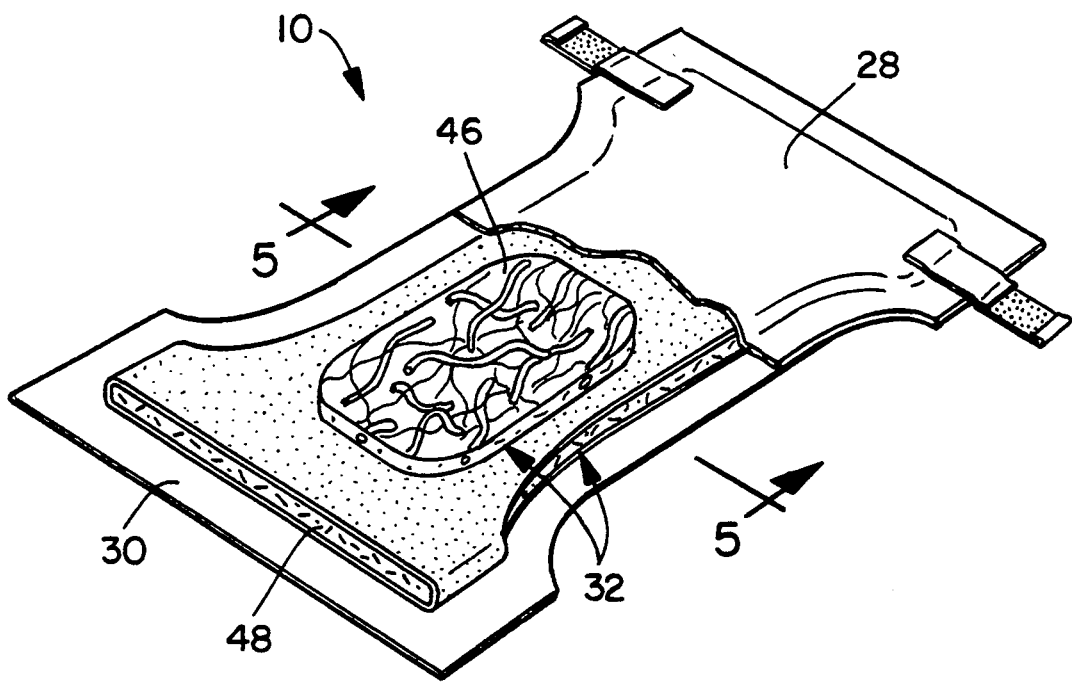
FIG. 4 is a perspective view of a diaper having a dual-layer core of the present invention.

As representatively shown in FIGS. 4, retention portion 48 can be situated underlying the surge management portion 46 in target zone 44, and can substantially define the boundaries of absorbent structure 32. Preferably, the retention portion 48 comprises hydrophilic fibers, such as cellulosic fluff, mixed with absorbent gelling particles which have a high retention capacity even under compressive loads applied in use. In other alternative arrangements, retention portion 48 may comprise a mixture of superabsorbent hydrogel particles and synthetic polymer meltblown fibers, or a mixture of superabsorbent particles with a fibrous coform material comprising a blend of natural fibers and/or synthetic polymer fibers.

Suitable absorbent gelling materials can be inorganic materials such as silica gels or organic compounds such as cross-linked polymers. Cross-linking may be by covalent, ionic, Van der Waals, or hydrogen bonding. Examples of absorbent gelling material polymers include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone and the like. Further polymers suitable for use in the absorbent structure include hydrolyzed, acrylonitrile grafted starch, acrylic acid grafted starch, polyacrylates and isobutylene maleic anhydride copolymers or mixtures thereof. Other suitable hydrogels are disclosed by Assarson et al. in U.S. Pat. No. 3,902,236 issued Aug. 26, 1975. Processes for preparing hydrogels are disclosed in U.S. Pat. No. 4,076,663 issued Feb. 28, 1978 to Masuda et al. and U.S. Pat. No. 4,286,082 issued Aug. 25, 1981 to Tsubakimoto et al.

As mentioned previously, the absorbent gelling material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 50 microns to about 1 millimeter. "Particle size" as used herein means the weighted average of the smallest dimension of the individual particles.

Where retention portion 48 comprises a mixture of absorbent gelling particles and cellulosic fluff, the retention portion may, for example, be densified to a density within the range of about 0.08–0.3 grams per cubic centimeter, and may contain about 5–70 percent by weight of the absorbent gelling material. In addition, the basis weight of the resultant web can range from about 200 to 3000 gsm. With reference to diaper articles, the density of the retention portion 48 is calculated from its basis weight and thickness, and is measured on newly unpacked, unfolded and desiccated diapers. For measuring bulk thickness to calculate densities, a suitable device is a TMI foam thickness gauge, Model No. TM1-49-21 or its equivalent. The apparatus is supplied by Testing Machines, Inc. of Amityville, N.Y.

Attempts to ameliorate gel blocking in typical fluid retention structures comprising mixtures of hydrophilic fiber and gelling material have employed a densification of such absorbent structures to ostensibly enhance the liquid wicking rate along the general plane of the structure (X-Y direction) as a result of a higher capillary force created by the smaller pore sizes within the matrix of densified fibers. Although densifying the absorbent structure does reduce the bulk thickness of the structure, the higher density may excessively reduce the rate of liquid intake.

In particular, the densification of the retention portion 48 can reduce the rate of liquid movement into the retention portion 48 along the thickness dimension, which is the direction normal to the general X-Y plane of the article (i.e., the Z-direction). It is believed that as higher concentrations of absorbent gelling material are located in the area of desorption underneath the surge management portion 46, a greater gel blocking effect may be created thereby reducing the liquid intake rate. Preferably, the materials in target zone 44 incorporate reduced amounts of absorbent gelling material, thereby reducing the incidence of gel-blocking in this zone and improving the liquid intake rate.

The surge management portion 46 can be of any desired shape consistent with the absorbency requirements of the absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between the surge management portion 46 and the retention portion 48 so that the relative capillarity difference between the portions can be fully utilized. In preferred embodiments, such as shown in FIGS. 3–6 and 8–9, the surge management portion can be oval-shaped with a top surface area of about 45 square inches (about 290 cm$^2$).

The surge management portion 46 should have an operable level of density and basis weight to quickly collect and temporarily hold liquid surges, and to transport the liquid from the initial entrance point to other parts of the absorbent structure 32, particularly the retention portion 48. This configuration helps prevent the liquid from pooling and collecting on the top sheet 28, thereby reducing the feeling of wetness by the wearer.

Surge management portion 46 preferably has a generally uniform thickness and cross-sectional area. Alternatively, a configuration can be used wherein the bodyside surface area of the surge management portion is greater or less than the surface area of a section taken along an X-Y plane located below the bodyside surface of the surge management portion.

With reference to FIG. 2, surge management portion 46, can be a separately formed absorbent layer, which lies on top of the retention portion 48. Thus, the surge management portion 46 need not comprise the entire thickness of the absorbent structure 32. It should be understood, however, that the surge management portion 46 could optionally extend the entire thickness of the absorbent structure 32 so that the capillary flow of liquid into retention portion 48 occurs primarily in the generally sideways (X-Y) direction.

Although the surge management portion 46 may be positioned anywhere along the absorbent structure 32, it has been found that the surge management portion 46 may function more efficiently when it is offset toward the front waistband of the garment and transversely centered within the front section 40 of the absorbent structure 32. Thus, the surge management portion 46 is approximately centered about the longitudinal center line 58 of the absorbent structure 32, and positioned primarily in the central region 54 of the front section 40 of the absorbent structure 32. In the illustrated embodiment, none of the surge management portion 46 is located in the ear regions of 50 and 52.

The generally forward, offset positioning of the surge management portion 46 can be defined by specifying the percentage of the top surface area of the surge management portion 46 which is found forward of a particular reference point, such as transverse centerline 24, along the length of the absorbent structure 32. The positioning of the surge management portion 46 can alternatively be defined with respect to the volume of the surge management portion positioned forward of a reference point.

As shown in FIGS. 2 and 4–6, the surge management portion 46 may comprise a separate layer which is positioned over another, separate layer comprising the retention portion, thereby forming a dual-layer core arrangement. The surge management portion serves to quickly collect and temporarily hold discharged liquids, to transport such liquids from the point of initial contact and spread the liquid to other parts of the surge management portion, and then to eventually release such liquids into the layer or layers comprising the retention portion 48. In the shown embodiment, the layer comprising the surge management portion is substantially free of absorbent gelling material.

Figure 12:
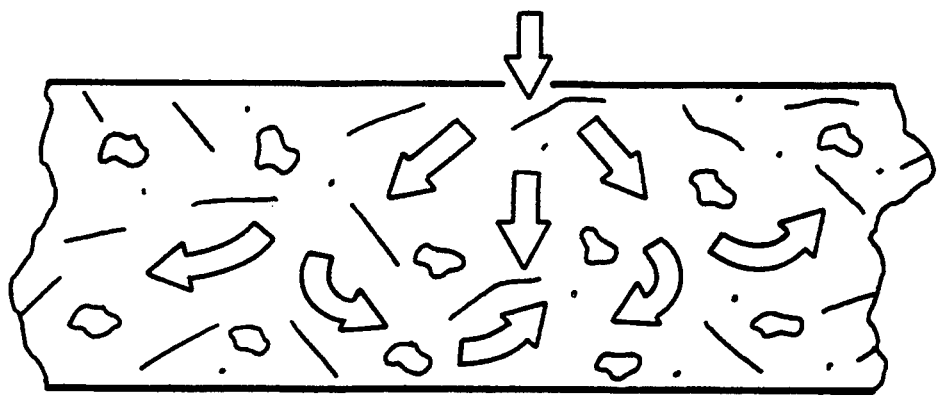
FIG. 12 is a schematic cross-sectional view of a conventional prior art diaper having absorbent core of hydrophilic fiber mixed with absorbent gelling material, during an initial fluid surge.
Figure 13:
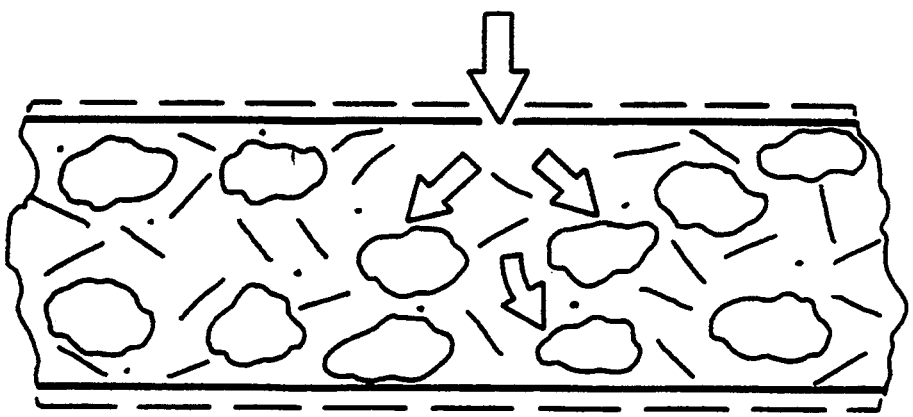
FIG. 13 is a sequential view showing the conventional prior art diaper core of FIG. 13 in a deteriorated state following one or more successive fluid surges.

Surge management portion 46 may, however, contain a very small amount of particulate gelling material to help acquire an initial liquid surge, but the amount should not be excessive. As illustrated in FIGS. 12 and 13, when excessive amounts of particulate absorbent gelling material are maintained in the target zone 44, the particles can cause the structure to retain and hold unacceptably high amounts of the liquid. Further, the transport of liquids away from the target zone 44 to other sections of the absorbent structure 32, particularly the retention portion 48, can be undesirably impaired.

The dual-layer arrangement can be of any desired shape consistent with comfortable fit. Suitable shapes include, for example, circular, rectangular, trapezoidal, oblong, hourglass-shaped or oval. With reference to FIG. 5, the entire absorbent structure 32, or any individual portions thereof, such as the retention portion, can be wrapped in a hydrophilic high wet-strength envelope web, such as a high wet strength tissue or a synthetic fibrous web, to minimize the potential for particles of absorbent gelling material to migrate out of the absorbent structure 32, particularly out of the retention portion 48. Such overwrapping web can also increase the in-use integrity of the dual layer absorbent structure. The web can, in fact, be glued to the absorbent structure 32 and to other components of the product construction.

Figure 8:
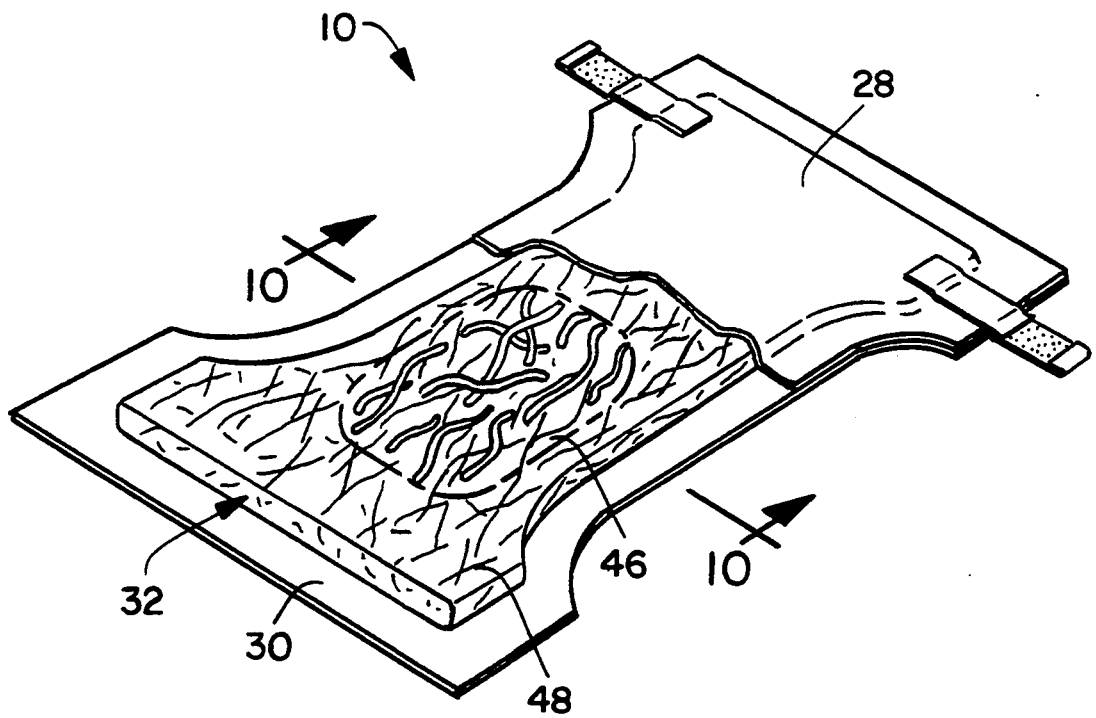
FIG. 8 is a perspective view of an alternative embodiment of the diaper of the present invention.
Figure 9:
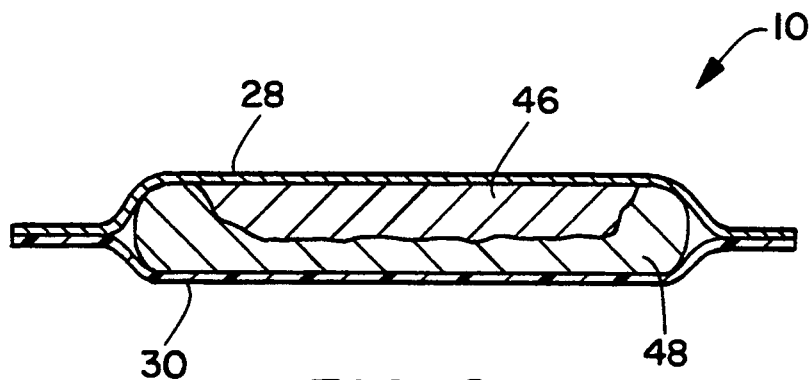
FIG. 9 is a cross-sectional view of the integrally formed absorbent structure of the diaper of the present invention, taken along sectional lines 10—10 of FIG. 9.

With reference to FIGS. 8 and 9, the absorbent structure of the present invention may advantageously comprise an integrally formed arrangement composed of non-uniform, differentially-configured fibrous sections wherein particular component sections, such as surge management portion 46 and retention portion 48, include fibers which are interwoven or otherwise entangled together at the fibrous interfaces between the components. Such an arrangement can advantageously improve the effectiveness of the liquid transport from the surge management portion and into the retention portion.

It is contemplated that a surge management portion constructed in accordance with the present invention will be tailored and adjusted to accommodate various levels of performance demand imparted during actual use. For example, mild urinary incontinence and menstrual flow pads involve different delivery rates, volumes and timing than infant urine insults. Moreover, the liquid in the surge can vary in terms of the liquid viscosity, surface tension, temperature, and other physical properties which could affect the performance of the fabric in the various actual product end usages.

With respect to absorbent articles, wherein reduced bulk or minimum cost may be important, the surge management and retention portions need not take on the entire overall shape of the garment. Rather, they could be generally configured and located to cover only the genital region of the wearer. For instance, both the surge management portion and the retention portion could be offset toward the front section of the garment outer cover 30.

It has been found that an effective fabric for constructing the surge management portion can be distinctively characterized by some or all of the following qualities: (a) a resilient structure having a selected basis weight; (b) an appropriate amount of total fiber-surface-area within the internal structure of the fabric; (c) a balance of fiber-surface-areas which are wettable and non-wettable; and (d) an appropriate distribution of the fibers within the volumetric space defined by the surge management portion. More particularly, the surge management portion can incorporate distinctive parameters which help characterize the liquid capillarity and other features of surge management portion 46. The parameters include the total amount of fiber-surface-area per standard unit of fabric; the amount of wettable-surface-area of such fibers per standard unit of fabric; a total-wettable-surface-area multiplied-by-density parameter; and a total-nonwettable-surface-area-multiplied-by-density parameter.

Resiliency and Basis Weight

A resilient fabric structure allows the fluid surge management portion of the present invention to:
1. stay open under load, to maintain void volume in the fabric;
2. resist collapsing when wetted to better release liquid and to better allow the fabric to be desorbed; and
3. be regenerating after being wetted to preserve void volume capacity for successive insult(s).

A particular embodiment of the present invention which provides desired levels of resiliency is a fabric comprising a selected proportion of relatively larger, stiffer fibers, such as the bonded-carded-web of Example 1.

The basis weight of surge management portion 46 is at least about 60 grams per square meter, and preferably is at least about 90 gsm to help provide the total void volume capacity desired for effective operation. In a particular aspect of the invention the basis weight is within the range of about 60–3000 gsm and preferably is within the range of about 90–3000 gsm to provide further advantages. In a further aspect of the invention, the surge management portion has a basis weight which is at least about 100 gsm, and preferably is within the range of about 100–3000 gsm to provide improved effectiveness.

The amount of basis weight is important for providing a total holding capacity which is adequate to temporarily retain the amount of liquid that is typically discharged by a wearer during a single surge/insult of liquid into the absorbent article. For instance, the material of Example 9 had inadequate basis weight, and had insufficient overall, total holding capacity to provide the desired temporary reservoir for suitably containing a typical amount of liquid surge. Such a configuration can result in excessive pooling of liquid against the wearer's skin or excessive run-off of liquid.

It will be readily apparent that absorbent articles requiring more surge capacity may also require proportionally greater amounts of surge management material. The surge management material, however, need not be of uniform basis weight throughout its areal extent, but instead can be arranged so that some sections have more surge management material compared to other sections. For the purposes of the present invention, the effective basis weight will be the weight of the surge management material divided by the area over which the surge management portion extends.

Surface Area

Figure 7A:
FIG. 7A is a representative photo-micrograph of a fibrous structure comprising the surge management portion of the present invention.
Figure 7B:
FIG. 7B is another representative photo-micrograph of a fibrous structure comprising the surge management portion of the present invention.

Liquid ordinarily flows along fiber surfaces, and the fiber surfaces are the usual transport routes to the void volume defined by the interfiber spacings of the fabric structure. By properly selecting the amounts and spatial arrangements of the wettable and nonwettable fiber surface areas per standard unit of fabric, the fluid access to the void volume of the material can be improved without adversely affecting the fluid release characteristics. Referring to the photomicrographs shown in FIG. 7A and 7B, a preferred fabric for the surge management portion can comprise a generally homogeneous blend of fine small diameter fibers intermingled with stiffer, larger diameter fibers. The finer the fiber size, the greater the available surface area per unit weight. Therefore, increased surface area is generally provided by using more fibers and finer fibers. High amounts of wettable surface area per unit weight of fabric can also be provided by fibrous webs composed of relatively large fibers with a high wettable surface area per unit weight, e.g. wood pulp fluff fibers. Although larger, stiffer fibers can enhance the ability of the material to maintain the desired structure when wetted and subjected to compressive forces, such as the compressive forces typically applied by the wearer of the garment during use, they may adversely affect tactile properties of the fabric and may not adequately increase the fiber surface area.

In a particular aspect of the invention, surge management portion 46 has a total fiber-surface-area value within the range of about 5–90 square meters per 100 grams of surge management material. In a further aspect of the invention, the surge management portion has a total fiber-surface-area value within the range of about 5–54 m$^2$ per 100 grams of surge management material, and in yet another aspect of the invention, the surge management portion has a total fiber-surface-area value within the range of about 12–54 m$^2$ per 100 grams of surge management material to provide further advantages.

The "fiber-surface-area" distributed within a particular quantity of surge management material can be determined by employing an image analysis technique which will be described in detail herein below. The fiber-surface-area values of surge management materials composed of fibers with modified, nonuniform cross-sections can be determined by employing the well known BET method which is described by Brunauer, Emmett and Teller, *Journal of the American Chemical Society*, 60,309 (1938), and which is hereby incorporated by reference into the present description.

The surge management portion can be a mixture of wettable and nonwettable fibers or can be composed entirely of wettable fibers. An appropriate fabric for the surge management portion should have a selected amount of wettable fiber surface area (SA$_w$) to (a) initially attract liquid into the fabric structure, (b) help provide rapid fluid uptake, and (c) help fill the void volume capacity of that fabric structure.

Figure 10:
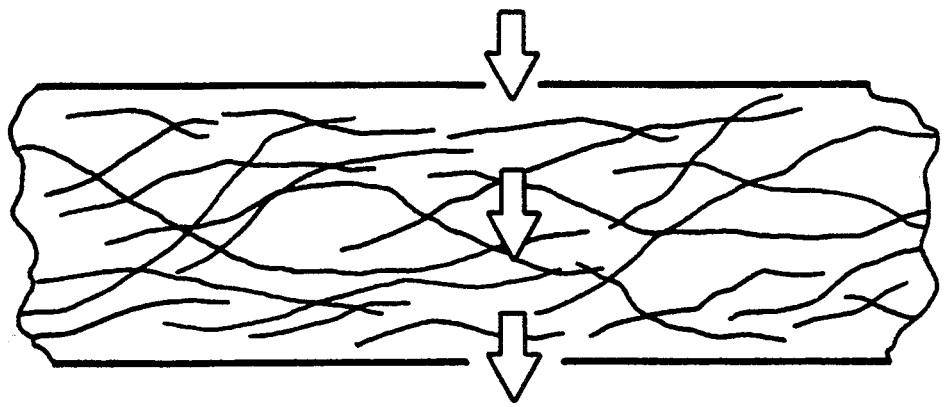
FIG. 10 is a schematic sectional view illustrating the fluid path through a typical prior art body-side liner.

Each incidence of liquid surge should "linger" in the fabric structure of the surge management portion long enough to occupy at least a part of its void volume capacity, instead of simply passing through in a relatively straight-line path. As illustrated in FIG. 10, a conventional layer of material can allow a substantially uninterrupted passage of liquid in a generally straight-line path without lingering in the structure prior to its release from the structure (large arrows).

Figure 11A:
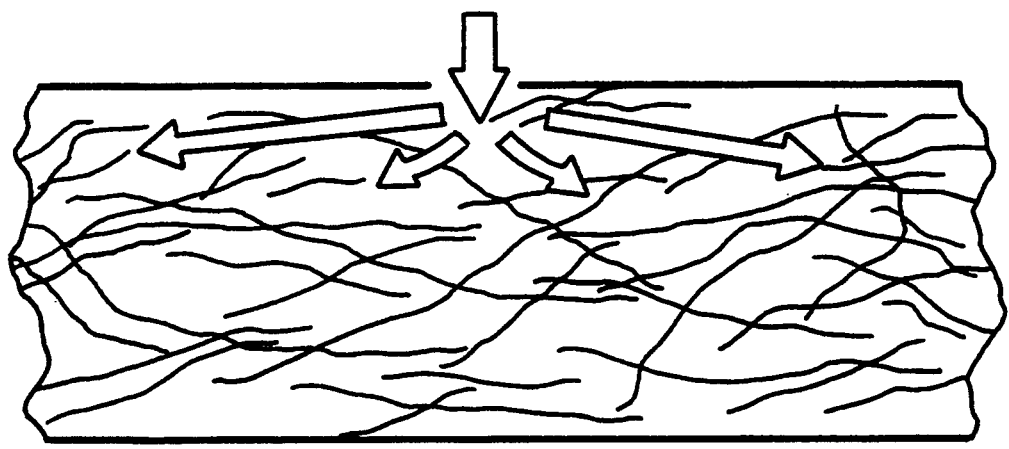
FIG. 11A is a schematic sectional view illustrating the movement of liquid which temporarily occupies the void volume capacity of a fibrous structure used for the surge management portion of the present invention.
Figure 11B:
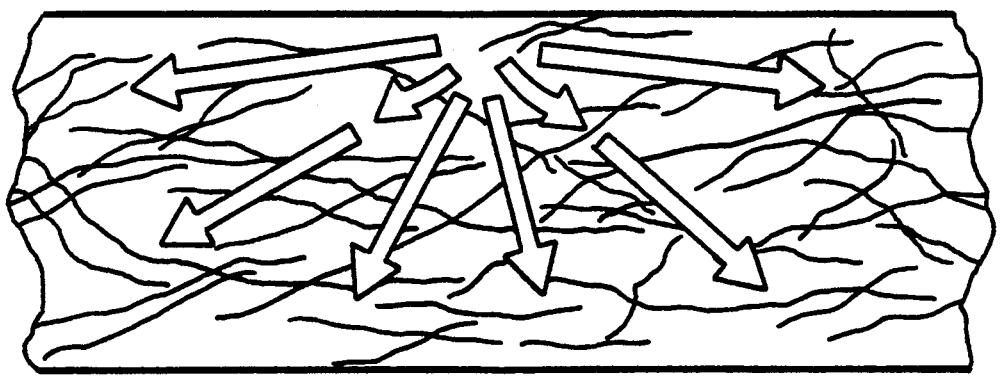
FIG. 11B is a second schematic sectional view further illustrating the movement of liquid which temporarily occupies the void volume capacity of a fibrous structure used for the surge management portion of the present invention.
Figure 11C:
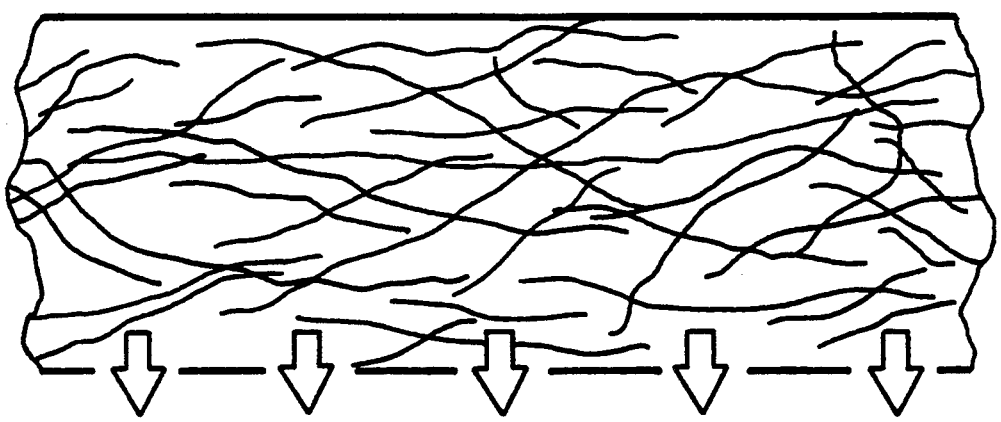
FIG. 11C is a third schematic sectional view illustrating the further movement of liquid which temporarily occupies the void volume capacity of a fibrous structure used for the surge management portion of the present invention.

The surge management portion of the invention can advantageously provide for a rapid uptake of the liquid surges (FIG. 11A) delivered onto the target zone and also allow a spreading of the liquid through the void volume of its structure (FIG. 11B) to temporarily fill it. The surge management portion can then be desorbed after a certain, limited period of time (FIG. 11C) through the operation of an underlying or surrounding liquid retention portion (not shown). Thus, the liquid surge can "linger" in the fabric structure to occupy the void volume for a discrete, transitional period instead of simply passing directly through in a generally straight-line path.

Wettable Surface Area (SA$_w$)

In a particular aspect of the invention, the surge management portion comprises a fibrous material having a wettable fiber-surface-area (SA$_w$) which is greater than zero and not more than about 70 square meters/100 grams of the surge management material. Preferably the surge management material has a wettable fiber-surface-area value which is greater than zero and not more than about 54 square meters per 100 grams of fabric. To provide further advantages, the wettable fiber-surface-area value is not less than about 3 and not more than about 54 square meters per 100 grams of fabric.

The total wettable surface area must be greater than zero so that some degree of wettability is present to initiate fluid penetration into the fabric structure and utilize its void volume capacity. With reference to Table 2 set forth herein below, Example 10 has no wettable surface area and exhibits excessively high penetration time values and low void capacity values. For fibrous structures having a wettable surface area of greater than 70 square meters per 100 grams of fabric there can be too much wettable surface attracting fluid, thus not allowing the structure to desorb or release liquid to other sections of an article. For instance, see Example 13.

The requirement for wettable fiber surface area can be met by using naturally wettable fiber components with measured contact angles of less than 90° in the fabric structure of the surge management portion. Such fiber materials include cotton, rayon and wood pulp. Other suitable fiber materials can be inherently wettable synthetic polymers; hydrophilized or surface treated polymers, etc.; or materials having permanent, i.e., nonmigratory, surface treatments applied to nonwettable substrate materials, for example, polypropylene, to reduce the contact angle below 90°.

Wettable Surface Area Times Density [(SA$_w$)*D]

In another aspect of the invention, surge management portion 46 can be characterized by a wettable fiber-surface-area-times-density [(SA$_w$)*D]$_3$ which is greater than zero and not more than about 7 m$^2$/100 cm$^3$. Preferably the wettable fiber-surface-area-times-density value is not more than about 5m$^2$/100 cm$^3$, and more preferably, is not more than about 4.0 m$^2$/100 cm$^3$ to provide improved effectiveness.

This structural parameter indicates how closely together the wettable surfaces of the structure are located. The value of this parameter should be greater than zero to insure that some wettable surface area is present to initiate rapid liquid penetration. A lower value for this parameter indicates that the wettable surface areas are somewhat spread out in the fabric structure. In contrast, a higher value would indicate that the wettable surface areas are fairly close together. When this value is too high, the wettable surface areas are so close together that the structure has strong affinity for liquids, and the liquids are not readily desorbed. As a result, the surge management portion may not adequately release the liquid surge to the desorbing retention portion. For example, the wettable surface area times density value

[SA$_w$*D] for Example 11 is excessively high. As a result, the fabric is unable to sufficiently release the fluid surge, and exhibits excessively high residual values.

Non-wettable Surface Area (SA$_{nw}$) Times Density, [(SA$_{nw}$)*D]

In a further aspect of the invention, surge management portion 46 has a nonwettable fiber-surface-area (SA$_{nw}$)-times-density value, [(SA$_{nw}$)*D], which is not more than about 1.1 m$^2$/100 cm$^3$. Preferably, the non-wettable fiber-surface-area-times-density value is not more than about 0.71 m$^2$/100 cm$^3$ to provide improved performance.

This parameter indicates how closely together the nonwettable, fibrous components are placed in the fabric structure. The parameter value can be zero, such as when the fabric is composed of 100 percent wettable fibers. A low value indicates the nonwettable surface areas are somewhat spread-out, and a higher value indicates the nonwettable surface areas are fairly close together. When this value is above about 1.1, m$^2$/100 cm$^3$, the nonwettable components may be too close together, hindering liquid penetration. This can excessively increase the amount of time required for the liquid to penetrate into the fabric structure, and the fabric may not have a sufficiently rapid uptake of the liquid. Likewise, a higher value for this parameter can indicate that the pores between the nonwettable fiber surfaces are tightly closed. As a result, the fabric structure may not be able to readily release fluid into a desorbing, retaining portion. For instance, Example 12 has a high nonwettable fiber-surface-area-times-density value, and does not sufficiently release liquid to a desorbing material. In addition, the material of Example 12 exhibits excessively high values for uptake time, particularly on repeat insults.

Total Surface Area (SA$_t$)

In a further aspect of the invention, surge management portion 46 has a total fiber-surface-area (SA$_t$) which is not less than about 5 and not more than about 90 square meters per 100 grams of surge management material. Preferably, the surge management portion has a total fiber-surface-area value of not less than about 5 and not more than about 54 square meters per 100 grams of surge management material to provide improved performance. To provide further advantages, the surge management portion has a total fiber-surface-area value of not less than about 12 and not more than about 54 m$^2$ per 100 gm of the surge management material.

Higher total surface area values indicate that the fabric structure can retain too much fluid, i.e., the fabrics exhibit excessively high residual values due to poor desorption performance. The structures do not adequately release the liquid surges into the retention, storage section of the absorbent structure. For instance, Example 13 illustrates this poor desorption. High total fiber-surface-area values can occur when wettable and/or nonwettable components are present in the maximum of each allowable range. Thus, the total surface area (SA$_t$) parameter can indicate whether a total blend of wettable and nonwettable fibers is balanced properly within the structure.

FABRIC DENSITY DETERMINATIONS

Density measurements can be taken using a TMI foam thickness gauge Model No. TMI-49-21, supplied by Testing Machines, Inc. of Amityville, N.Y. This type of gauge allows bulk thickness measurements to be made while exerting a very low compressive force of about 0.05 psi (about 0.34 kPa) on the fabric.

PENETRATION RATE DESORPTION (PRD) TEST

Figure 14:
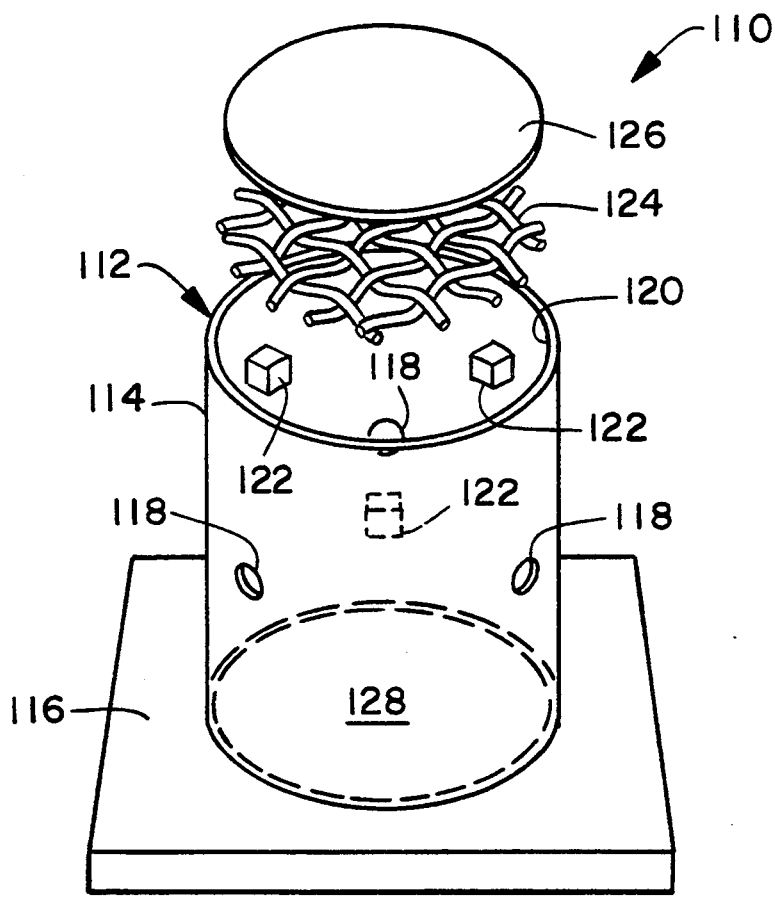
FIG. 14 is a perspective view of an apparatus for carrying out the Penetration Rate Desorption (PRD) Test procedure used to characterize absorbent structures having the surge management portion of the present invention.
Figure 15:
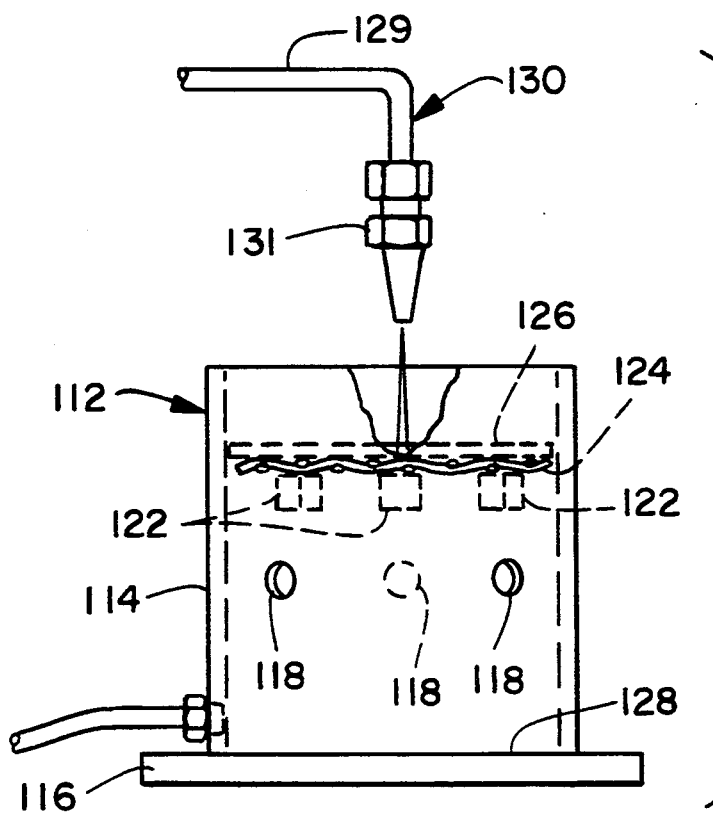
FIG. 15 is a side elevational view representatively showing the PRD Test apparatus of FIG. 15 in operation.

This test allows the testing and screening of fabrics to determine whether the structures thereof provide required values for particular surge management parameters. Further, it allows the testing of individual fabrics whereby the performance of the fabrics themselves can be measured without variables being introduced by other components, such as lofty liner fabrics which are often placed on the body side surface of absorbent structures to aid in dryness, etc. The PRD test is conducted using liquid flow conditions (e.g., amount, flow rate and velocity) which closely simulate conditions experienced by a surge management portion during use. The fluid used in the PRD test is a synthetic urine, such as described in U.S. Pat. No. 4,699,619, delivered at a temperature of about 37° C. (about 98.6° F.). With reference to FIG. 14, a testing apparatus generally shown at 110, includes a test holder base 116 and a hollow tube, generally indicated at 112. The tube is composed of, for example, Lucite® or other clear strong material, which allows a view of the liquid penetration during testing. The tube 112 has a 3 inch inner diameter and a wall thickness of about 0.25 inches. The tube stands vertically on end and is approximately 6 inches tall. The vertical tube wall 114 is sealed to a flat base 116 which is composed of a similar clear material, for example Lucite®, and which measures about 6 inches by 6 inches square. Three (3) holes 118, approximately 0.50 inches in diameter, are drilled through the wall 114 of tube 112 to allow air circulation to the inside of the tube 112 and to avoid back pressure buildup inside the tube. These holes 118 are equally spaced around the circumference of the tube at relative positions of 0°, 120° and 240°, and are placed 3 inches down from the upper edge 120 of the tube 112. Three small rectangular pieces composed of a clear material, for example Lucite®, and having dimensions of 0.375 inches wide by 0.75 inches long by 0.25 inches thick are mounted to the inside wall surface of tube 112 in a vertical position, forming projections 122 extending into the inner diameter space of the tube 112. The three projections are placed 1.5 inches down from the upper edge 120 of the tube at 60°, 180° and 300° intervals around the circumference of the tube 114. The projections 122 are staggered from the position of the air holes 118 as illustrated in FIG. 14. A three inch diameter round piece of a woven or an extruded plastic mesh screen 124 (2 mesh per inch) is placed horizontally inside the upper portion of the tube to rest on the projections 122, as shown in FIG. 15. If desired, an annular support ring (not shown) may be employed to help support the peripheral edges of the mesh screen. The support ring would rest upon projections 122 and the edges of the mesh screen would, in turn, rest upon the support ring. The support ring is constructed and arranged so as to not impede the movement of liquid through the test sample. The projections 122, the plastic screen 124 and the supporting ring act as a sample support system.

Referring to FIG. 15, synthetic urine for the test is supplied at a rate of 15 milliliters per second through a miniature 12-volt DC miniature gear pump (not shown) manufactured by Cole Parmer Instrument Company of Chicago, Ill. The liquid which is to be delivered to the fabric sample, passes through a nozzle assembly 130 comprising a No. 316 stainless steel tube 129 fitted with a nozzle tip 131 having an inner diameter of 0.103 inches. The temperature of the synthetic urine is suitably controlled to provide a temperature of about 37° C. (about 98.6° F.) at the time of delivery to the fabric sample. The nozzle and pump are configured to impart an initial velocity of 210 centimeters per second to the fluid. The nozzle tip is directed downwardly, along a direction perpendicular to the fabric surface being tested, and is located approximately one inch from the upper surface of the test fabric.

Procedure:

A preweighed, circular sample 126 of test fabric measuring 3 inches in diameter is placed inside the tube 112 on the plastic screen 124. A standard test amount of one hundred (100) milliliters of synthetic urine is inputted to the fabric at a volume rate of 15 milliliters per second through nozzle assembly 130. The time required for all liquid to penetrate into the surface of the sample 126 is measured in seconds, beginning from the initiation of the delivered liquid insult, and is recorded. Typically, some liquid is held within the sample 126, and some liquid passes through the sample and is collected in the bottom 128 of tube 112. The sample 126, along with the liquid held therein, is then removed from holder 112 and weighed.

The sample 126 is then placed on a 4 inch by 4 inch square desorption pad composed of cellulosic wood pulp fluff mixed with superabsorbent particles. To this purpose, the desorption pad can comprise a mixture of softwood fluff designated "CR-54," available from Kimberly-Clark Corporation, and a hardwood pulp fluff designated Longlac 19 ® also available from Kimberly-Clark Corporation which have been air-laid according to conventional techniques to form a fibrous web. About 12 percent of the dry weight of the desorption pad comprises superabsorbent particles available from Hoechst-Celanese Corporation as IM1500. The particles are mixed with the air laid fluff fibers to form a pad having a density of about 0.1 gm/cc and a basis weight of about 1400 gsm. The desorption pad should be constructed and arranged such that after an immersed saturation with synthetic urine under free-swell conditions for 5 min, the pad retains at least 10 gm of synthetic urine per gram of desorption pad after being subjected to an air pressure differential (vacuum suction) of about 0.5 psi (about 3.45 kPa) applied across the thickness of the pad for 5 min. A suitable weight (not shown) is then placed on the fabric sample 126 to apply a pressure of 0.25 psi over the entire sample to desorb the liquid from sample 126 and into the desorption pad positioned immediately below the sample. After 15 minutes, the weight is removed and the sample 126 is weighed again. This completes the first cycle. The desorption pad is discarded, and a fresh desorption pad is obtained for the next cycle of the procedure. The sample is then returned to supporting screen 124 substantially without further drying or desorption of the sample, and the testing cycle (introducing liquid, weighing, desorbing and weighing) is repeated two more times for a total of three cycles. The three uptake-and-desorption cycles are completed within a period of 60 min.

Measurements and Calculations

During the PRD Test procedure the following ten (10) items of data are measured for each fabric sample tested. Sample weights are designated in brackets:
1. The initial weight of the sample: [A].
2. Three (3) penetration times, i.e. one for each of the 100 milliliter synthetic urine insults.
3. Three (3) saturated sample weights, that is, one weight after each insult: $[B_n]$; n=1,2,3.
4. Three (3) final sample weights, that is, one weight after each desorption cycle: $[C_n]$; n=1,2,3.

Nine (9) values are to be determined by the PRD Test, that is, values for each of three (3) parameters measured during each of the three (3) successive synthetic urine insult cycles, are calculated as follows:
1. Three uptake time values are measured and determined directly from the penetration times (in seconds).
2. Temporary loading values measured as grams of fluid held due to insult (n) per gram of fabric are calculated as:

$$(\text{Temporary Loading})_n = \frac{[B_n] - [A]}{[A]} \; ; n = 1,2,3$$

3. Release of fluid, residual values measured as grams of fluid remaining after desorption (n) per gram of fabric, are calculated as:

$$(\text{Residual})_n = \frac{[C_n] - [A]}{[A]} \; ; n = 1,2,3$$

The uptake time value is an indicator of the liquid uptake rate for a fabric sample. The temporary loading value is a measure of the transitional reservoir capacity of a sample, and the residual value is a measure of the release characteristics of the fabric sample.

If the uptake time value is too high, the material of the surge management portion can be adjusted by increasing the proportion of the wettable-fiber-surface-area $(SA_w)$ of the fabric and/or by decreasing the density of the bulk fabric. If the temporary loading value is less than desired, the material of the surge management portion can be adjusted by increasing the wettable-fiber-surface-area $(SA_w)$ of the fabric and/or by increasing the density of the bulk fabric. If the residual value is too high, the surge management material can be adjusted by decreasing the wettable-fiber-surface-area $(SA_w)$ and/or by reducing the density of the bulk fabric. It should be understood that the increase or decrease of the proportion of wettable-fiber-surface-area will cause a corresponding but opposite change in the relative proportion of the nonwettable-fiber-surface-area $(SA_{nw})$ within the fabric material.

The fabric can also be adjusted to address various combinations of the uptake time, temporary loading and residual values. For example, if the uptake time value and the temporary loading value are not within desired ranges, the surge management material can be adjusted by increasing the wettable-fiber-surface-area of the fabric. As a further example, if the residual value and temporary loading value are not within desired ranges, the surge management material can be adjusted by decreasing the wettable-fiber-surface-area or by decreasing the density of the bulk fabric.

FIBER WETTABILITY DETERMINATIONS

The wettability of fibers can be determined using contact angle measurements on fibers. Repeat cycle, single fiber contact angle measurements using distilled water were performed with a Cahn Surface Force Analyzer (SFA222) and WET-TEK ® data analysis software. The SFA222 is available from Cahn Instruments, Inc., of Cerritos, Calif., and the WET-TEK software is available from Biomaterials International, Inc., of Salt Lake City, Utah. Fibers are tested through three measurement cycles, and the distilled water bath is changed between cycles one and two. Fibers are determined to be "wettable" if all three of the repeat cycles measure a contact angle of less than 90°. Otherwise, the fibers are deemed "nonwettable". The test instrument is operated in accordance with the standard operating techniques described in the Cahn SFA-222 System Instruction Manual supplied by the manufacturer.

FIBER SURFACE AREA MEASUREMENTS

Figure 16:
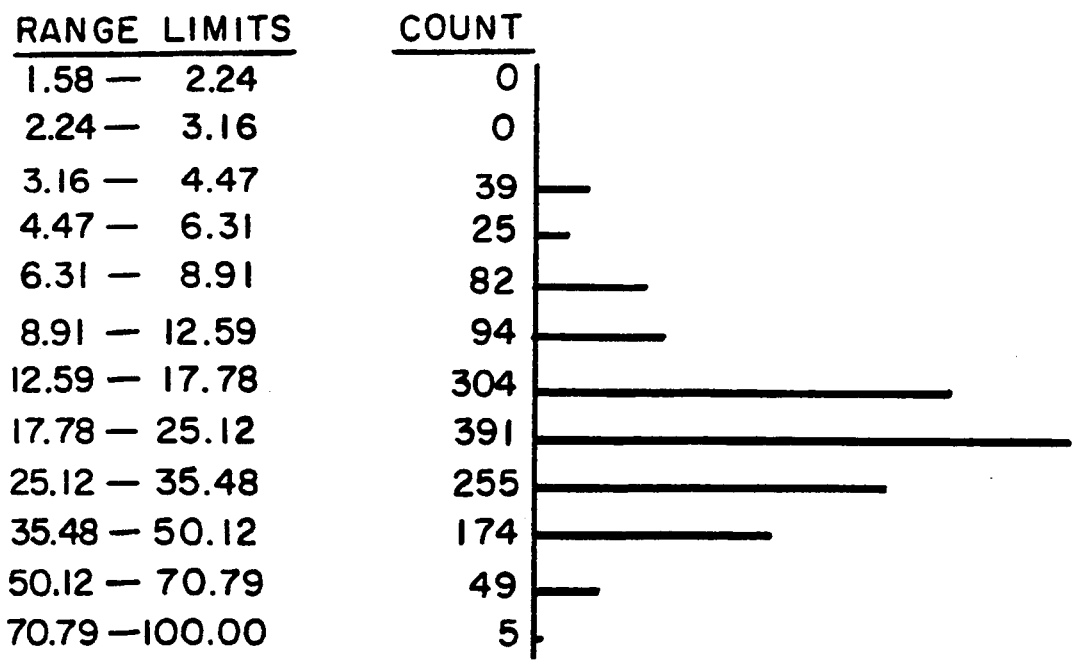
FIG. 16 is representative example of a histogram generated by the image analysis of a fibrous sample.

Surface areas of the fibers contained within a fabric can be determined by a combination of mathematical and empirical methods, depending upon the fibrous composition. Surface areas of fabrics composed of round cross-section, staple fibers can be calculated directly. Fabrics composed of round cross-section melt extruded fibers (e.g. meltblown and spunbond fibers), can be examined with known image analysis techniques to achieve a fiber diameter distribution plot, or histogram (e.g. FIG. 16). From the histogram, calculations can be completed to determine the surface area values of the fibers. The fiber-surface-areas within webs composed of modified cross-section fibers, such as modified cross-section staple fibers, modified cross-section melt extruded fibers and/or non-uniform cross-section cellulosic fibers can be measured by the BET method of Brunauer, Emmett and Teller, *Journal of the American Chemical Society*, 60, 309 (1938).

The fiber size histograms can be obtained by employing conventional image analysis techniques, which are well known in the art. In a suitable technique, six random ¾ in × 1 in samples are taken of a selected fabric and prepared by coating them with gold/palladium employing a conventional sputter coater, such as a Balzer's Union Model SDC-040 Sputter Coater. Two 4 in × 5 in, backscatter electron photomicrographs are taken of each of the six samples using instant, black and white film, such as POLAROID Type 52 or 55 film. A suitable electron microscope for this purpose is a JEOL Model JSM 840, which is distributed by Japanese Electro Optical Laboratories, Inc. located in Boston, Mass. For samples in which extruded fibers (e.g., meltblown fibers) are combined with other fibers (e.g., staple fibers or pulp fibers), the fields of view on the electron microscope are chosen at random until six photomicrographs with substantially no staple or pulp fibers are obtained (a total of 12 photomicrographs from the two samples of a selected fabric).

The magnification level is typically within the range of about 25X–500X, and is ordinarily selected to provide, with respect to the smallest fibers present in the sample fabric, images which measure approximately 0.5 mm in width. If, however, a fabric sample includes therein a particularly large range of fiber sizes such that the desired magnification of the smallest fibers also produces an excessive magnification of the largest fibers, a compromise magnification is employed. The selected magnification is chosen so as to provide a histogram having good "end group" stability, as discussed herein below.

Each of the photomicrographs is placed on the macroviewer of a suitable image analyzing device, such as a Quantimet 900 Image Analysis System, which is distributed by Cambridge Instruments, a company located in Deerfield, Ill. There are two fields of view taken on each photomicrograph with each field of view covering approximately one-third of the area of the photomicrograph. Each field of view is divided into 9 subregions comprising a 3×3 grid. Within each subregion, the individual fibers are identified and typically appear as white fibers on a black background. The diameter of an individual fiber is measured with a light pen by drawing a "slice" length from edge to edge across the width of the viewed fiber. The slice should be drawn substantially perpendicular to the tangent line which intersects the point on the edge of the fiber at which the slice measurement begins. Care must be taken to avoid designating and measuring side-by-side fibers as a single large fiber. For round fibers, the slice lengths are taken to be the fiber diameters, and are compiled into a fiber diameter histogram.

This procedure is performed while using the EDIT/LINE mode on the Quantimet 900 System, and is performed on as many fibers as possible to reduce statistical biasing. Slice length measurements are performed on about 1000 fibers within each set of 12 photomicrographs. However, statistical stability of the surface area calculation can be achieved with fewer fiber counts on some samples. The statistical stability of the surface area can be determined by performing "end group checks" on the smallest and largest classes in the histogram. This is done by placing the counts in these classes into the adjacent class toward the "mode" class, and recalculating the surface area per unit weight. The percent change in the calculated fiber surface area should be less than 10%, and is preferably less than 5%.

Calculations of Fiber Surface Area

The fiber surface area per weight of a mass of fibers (SA) can be calculated as follows:

$$(SA) = \sum_i \left[ \frac{W_i}{100} * (SA)_i \right] \quad (1)$$

where
$(SA)_i$ = surface area per weight of fiber i
$W_i$ = weight percent of fiber i
However, for a given fiber the surface area per weight in square meters of fiber surface area per 100 grams of fiber is given by $$(SA)_i = \frac{L_i * d_i * \pi}{L_i * (d_i/4) * \pi * \rho_i} * \frac{(10^{-6} \text{ meter/micron}) * 100 \text{ g}}{(10^{-6} \text{ meter/micron})^2 * (10^6 \text{ cm}^3/\text{meters}^3)} \quad (2)$$

or $$(SA)_i = \frac{4 * 100}{\rho_i * d_i} \quad (3)$$

where
$L_i$ = total length of fiber i $d_i$ = diameter of fiber i in microns
$\rho_i$ = density of fiber i in g/cm$^3$ Therefore, from equations (1) and (3) the total surface area becomes $$(SA) = \sum_i \left[ \frac{W_i}{100} * \frac{400}{\rho_i * d_i} \right] \quad (4)$$

or $$(SA) = \sum_i \left[ \frac{4 * W_i}{\rho_i * d_i} \right] \quad (5)$$

For staple fibers $$den_i = \frac{wt_i}{9000 \text{ meters}} \quad (6)$$

where
$den_i$ = denier of fiber i
$wt_i$ = weight in grams of 9000 meters of fiber i
but $$wt_i = L_i * (d_i/2)^2 * \rho_i * \pi \quad (7)$$

Therefore, from equations (6) and (7)

$$den_i = (d_i/2)^2 * \pi * \rho_i * 9000 \text{ meters} * (100 \text{ cm/meter}) * (10^{-4} \text{cm/micron})^2 \quad (8)$$

or $$den_i = (d_i/2)^2 * \pi * \rho_i * 9 * 10^{-3} \quad (9)$$

Then, from equation (9)

$$d_i = [4 * den_i / (\pi * \rho_i * 9 * 10^{-3})]^{\frac{1}{2}} \quad (10)$$

or $$d_i = 11.894 * (den_i / \rho_i)^{\frac{1}{2}} \quad (11)$$

Therefore from equations (5) and (11)

$$(SA) = \sum_i \left[ \frac{W_i * 4}{\rho_i * 11.894 * (den_i/\rho_i)^{\frac{1}{2}}} \right] \quad (12)$$

$$(SA) = \sum_i \left[ W_i * \frac{0.3363}{(den_i * \rho_i)^{\frac{1}{2}}} \right] \quad (13)$$

Thus, for example, a blend of 50% by weight 3 denier polyester fiber with 50% by weight 3 denier polypropylene fiber would have a total fiber-surface-area-per-weight of:

$$(SA) = \frac{(50)(.3363)}{[(0.91)(3)]^{\frac{1}{2}}} + \frac{(50)(.3363)}{[(1.38)(3)]^{\frac{1}{2}}} \quad (14)$$

$$= 36.04 \text{ meter}^2/100 \text{ grams}$$

where $\rho_{polypropylene} = 0.91$ g/cm$^3$ $\rho_{polyester} = 1.38$ g/cm$^3$

With a material composed of extruded fibers having various, different fiber sizes, such as meltblown and spunbond fibrous webs, the fibers are examined with image analysis techniques to obtain a fiber diameter histogram. From the histogram, calculations are completed to sum the surface areas of each individual fiber diameter present. For example, the representative fiber size distribution histogram shown in FIG. 16 corresponds to the meltblown web of Example 2 which is set forth below in the Examples section. It is readily apparent that a frequency or Count % for each of the diameter range limits can be calculated from the histogram. The sum of the frequencies (Count %) of all fiber sizes equals 100.

In the case of webs composed of various fiber sizes, such as meltblown fibrous webs, where the weight percents of each fiber size cannot be measured directly, the weight percents can be determined from the fiber size distribution as follows:

The weight percent of fiber i of a particular diameter and polymer density, $W_i$, is given by $$W_i = \frac{100 * wt_i}{\sum_i wt_i} \quad (15)$$

If we assume that the count percent, $C_i$, of fiber of size $d_i$ and density $\rho_i$, as determined by image analysis, is given by $$C_i = 100 * \frac{L_i}{\sum_i L_i} \quad (16)$$

Then, from equation (16)

$$L_i = \frac{C_i}{100} * \sum_i L_i \quad (17)$$

But the total fiber length, $\Sigma_i L_i$, in a given material is constant. Therefore, $$L_i = B * \frac{C_i}{100} \quad (18)$$

Where B is a constant.
Therefore, from equations (7) and (18)

$$wt_i = B * \frac{C_i}{100} * (d_i/2)^2 * \rho_i * \pi \quad (19)$$

and from equations (15) and (19), the weight percent of fiber size and type i is given by $$W_i = \frac{100 * B * (C_i/100) * \pi * (d_i/2)^2 * \rho_i}{\sum_i [B * (C_i/100) * \pi * (d_i/2)^2 * \rho_i]} \quad (20)$$

or $$W_i = \frac{100 * C_i * d_i^2 * \rho_i}{\sum_i [C_i * d_i^2 * \rho_i]} \quad (21)$$

If all of the meltblown fibers are of the same polymer, the $\rho_i$ is constant and equation 21 becomes $$W_i = \frac{100 * C_i * d_i^2}{\sum_i [C_i * d_i^2]} \quad (22)$$

Hence the weight percent of each fiber size in a particular meltblown material can be calculated from the fiber size histogram for that material.

Thus, from equations (5) and (21), the fiber surface area of a meltblown material becomes $$(SA) = \frac{100 * \sum_i [(C_i * d_i^2) * (4/(\rho_i * d_i))]}{\sum_i [C_i * d_i^2]} \quad (23)$$

or $$(SA) = \frac{100 * \sum_i [C_i * 4 * d_i/\rho_i]}{\sum_i [C_i * d_i^2]} \quad (24)$$

Fiber counts obtained by image analysis and set forth in the resultant histogram are given for ranges of fiber sizes and not for individual fiber sizes. Therefore, for the purposes of the present invention, the surface area contributed by particular range of fiber sizes is determined by first assuming that all of the fibers have the diameter defined by one extreme of the range, and calculating a corresponding surface area value. Next, it is assumed that all of the fibers within the range have the diameter defined by the other extreme of the range, and a second corresponding surface area value is calculated. The two surface area values are then averaged to obtain the surface area value for that particular range of fiber sizes. This procedure is repeated for each fiber size range, and the results are summed to get the surface area value for the total sample.

For the calculations described above, the determination of surface areas has included the assumption that the fibers have substantially round, circular cross-sections. For other fibers, such as modified cross-section staple fibers, modified cross-section melt extruded nonwoven fibers and non-uniform cross-section cellulosic fibers, the fiber surface area values can be measured by the BET method referred to herein above. The BET technique involves the absorption of a mono-molecular layer of gas molecules on to the surface of the fibers. Calculations regarding the amount of gas present on the fibers yields a quantification of the fiber surface area values. This method has been used fairly routinely in the paper industry for fibrous webs, such as papers, fillers and filter materials.

Through the years, literature has cited a variety of softwood and hardwood pulp fiber surface area measurements ranging from 50 to 150 m² per 100 grams. For the purpose of sample demonstration, example fabrics using pulp fibers, such as pulp coform materials, have included an approximation of 100 m² of surface area per 100 grams of wood fiber.

The following examples are presented to provide a more detailed understanding of the invention. The particular materials and parameters are exemplary, and are not intended to specifically limit the scope of the invention.

EXAMPLES

A first group of preferred fabrics exhibited the following characteristics:
 (a) greater than 60 gsm basis weight;
 (b) a penetration, uptake time value of less than 12 seconds;
 (c) a temporary loading value per liquid surge of at least about 3 gm per gram of fabric;
 (d) a residual value of no more than 1.00 gm per gram of fabric.

Fabrics in the first grouping also exhibited the following characteristics:

(e) $0 < (SA_w) \leq \dfrac{70 \text{ m}^2}{100 \text{ gm fabric}}$ (f) $0 < (SA_w) * D \leq \dfrac{7 \text{ m}^2}{100 \text{ cm}^3 \text{ fabric}}$ (g) $(SA_{nw}) * D \leq \dfrac{1.1 \text{ m}^2}{100 \text{ cm}^3 \text{ fabric}}$ (h) $5 \leq (SA_t) \leq \dfrac{90 \text{ m}^2}{100 \text{ gm fabric}}$ It is again noted that for Examples 1-8 of the invention the requisite levels of performance for the parameters of uptake time, temporary loading and residual values were met for each of three successive liquid inputs administered in accordance with the PRD Test.

Another, second grouping of preferred fabrics for the surge management portion of the present invention exhibited the following characteristics:
 (a) greater than 90 gsm basis weight;
 (b) less than 10 seconds for the uptake time value;
 (c) a temporary loading value of greater than 6.0 gram per gram of fabric;
 (d) a residual value of less than 0.75 gm per gram of fabric.

Fabrics in the second grouping also exhibited the following characteristics:

(e) $3 \leq (SA_w) \leq \dfrac{54 \text{ m}^2}{100 \text{ g fabric}}$ (f) $0 \leq (SA_w) * D \leq \dfrac{5 \text{ m}^2}{100 \text{ cm}^3 \text{ fabric}}$ (g) $(SA_{nw}) * D \leq \dfrac{1.1 \text{ m2}}{100 \text{ cm}^3 \text{ fabric}}$ (h) $5 \leq (SA_t) \leq \dfrac{54 \text{ m}^2}{100 \text{ gm fabric}}$ Samples of fabrics which corresponded to the second grouping are Examples 1-4 and 6-8 set forth herein below.

Yet a third grouping of more preferred fabrics for the surge management portion of the present invention had the following parameters:
 (a) greater than 100 gsm basis weight;
 (b) an uptake time value of less than 8 seconds;
 (c) a temporary loading value of greater than 9 gram per gram of fabric;
 (d) a residual value of less than 0.5 gm per gram of fabric.

Fabrics which had the parameters listed for the third grouping also had the parameter values set forth immediately below:

(e) $3 < (SA_w) \leq \dfrac{54 \text{ m}^2}{100 \text{ g fabric}}$ operably function as improved surge management portions are not necessarily restricted to any given class of structures, e.g. bonded carded webs, meltblown webs, pulp coform webs, staple coform webs, etc.

The functional and structural parameters of the following Examples 1 through 13 are summarized in Tables 1 and 2 below.

TABLE 1

| Example No. | NonWoven Formation Technology | Basis Weight gsm | Density g/cc | Penetration Times (Sec) | | | G/G Load Upon Insult | | | G/G After Desorption | | |
|---|---|---|---|---|---|---|---|---|---|---|---|---|
| | | | | 1 | 2 | 3 | 1 | 2 | 3 | 1 | 2 | 3 |
| 1 | Bonded Carded Web | 211 | 0.034 | 6.4 | 6.2 | 6.8 | 14.33 | 15.71 | 13.28 | 0.29 | 0.23 | 0.23 |
| 2 | Meltblown | 213 | 0.070 | 6.7 | 6.8 | 6.6 | 10.75 | 9.25 | 9.17 | 0.29 | 0.28 | 0.29 |
| 3 | Meltblown | 216 | 0.111 | 6.8 | 6.8 | 6.5 | 8.44 | 7.85 | 7.78 | 0.41 | 0.40 | 0.38 |
| 4 | Pulp Coform | 194 | 0.037 | 6.6 | 6.6 | 6.7 | 17.27 | 14.25 | 14.11 | 0.48 | 0.41 | 0.41 |
| 5 | Bonded Carded Web | 223 | 0.045 | 6.7 | 6.6 | 6.9 | 6.17 | 3.80 | 3.28 | 0.13 | 0.15 | 0.12 |
| 6 | Staple Coform | 203 | 0.038 | 6.4 | 6.7 | 6.6 | 10.16 | 9.92 | 11.90 | 0.24 | 0.25 | 0.26 |
| 7 | Staple Coform | 183 | 0.041 | 6.7 | 6.9 | 6.9 | 18.25 | 17.12 | 16.97 | 0.61 | 0.72 | 0.56 |
| 8 | Staple Coform | 194 | 0.023 | 6.5 | 6.8 | 6.7 | 12.81 | 19.06 | 21.83 | 0.17 | 0.47 | 0.45 |
| 9 | Spunbonded | 26 | 0.112 | 6.6 | 6.9 | 6.7 | 9.16 | 10.15 | 10.28 | 0.29 | 0.31 | 0.45 |
| 10 | Melt-Sprayed | 239 | 0.098 | 11.9 | 14.4 | 14.1 | 0.73 | 0.92 | 1.02 | 0.07 | 0.14 | 0.14 |
| 11 | Melt-Sprayed | 143 | 0.124 | 10.5 | 11.1 | 10.8 | 8.98 | 7.51 | 7.55 | 2.37 | 2.35 | 2.41 |
| 12 | Pulp Coform | 108 | 0.053 | 9.4 | 13.8 | 17.1 | 21.89 | 15.06 | 14.10 | 5.08 | 4.38 | 5.08 |
| 13 | Pulp Fluff | 529 | 0.101 | 6.9 | 9.7 | 9.6 | 13.62 | 9.38 | 8.93 | 3.10 | 2.67 | 2.71 |

TABLE 2

| Example No. | Composition | Wettable Surf. Area m²/100 gms | Surf. Area * Density: | | Total Surf. Area (m²/100 gm) |
|---|---|---|---|---|---|
| | | | Wettable (m²/100 cc) | Nonwettable (m²/100 cc) | |
| 1 | 50% Polyester 40 den<br>35% Bleached Cotton 1.5 den<br>15% Chisso ES 1.5 den | 10.6 | 0.34 | 0.15 | 14.38 |
| 2 | 100% HYDROFIL Macro Fiber | 11.69 | 0.82 | 0.0 | 11.69 |
| 3 | 100% HYDROFIL Macro Fiber | 9.12 | 1.01 | 0.0 | 9.12 |
| 4 | 50% Pulp<br>50% Macro Fiber PP MB | 50.00 | 1.85 | 0.12 | 53.18 |
| 5 | 40% Polyester 40 den<br>25% Rayon 3 den<br>15% Polyester 6.5 den<br>20% Chisso ES 6 den | 7.93 | 0.36 | 0.13 | 10.82 |
| 6 | 50% HYDROFIL Micro Fiber MB<br>38% Polyester 25 den<br>12% Chisso ES 1.5 den | 10.75 | 0.41 | 0.71 | 12.48 |
| 7 | 30% Micro Fibers PP MB<br>56% Polyester 25 den<br>14% Chisso ES 1.5 den | 3.21 | 0.13 | 1.03 | 28.35 |
| 8 | 30% Micro Fibers PP MB<br>56% Polyester 25 den<br>14% Chisso ES 1.5 den | 3.21 | 0.07 | 0.58 | 28.35 |
| 9 | 100% Rayon Spunbond from Futamura Chemicals, Japan | 19.42 | 2.18 | 0.0 | 19.42 |
| 10 | 100% Macro Fiber PP MS | 0.0 | 0.0 | 0.74 | 7.60 |
| 11 | 100% Micro HYDROFIL MS | 73.77 | 9.15 | 0.0 | 73.77 |
| 12 | 30% Pulp<br>70% Micro Fiber PP MB | 30.0 | 1.59 | 2.32 | 73.68 |
| 13 | 100% Pulp (no Superabsorbent) | 100.0 | 10.1 | 0.0 | 100.0 |

(f) $0 < (SA_w) * D \leq \dfrac{4 \text{ m}^2}{100 \text{ cm}^3 \text{ fabric}}$ (g) $(SA_{nw}) * D \leq \dfrac{0.71 \text{ m}^2}{100 \text{ cm}^3 \text{ fabric}}$ (h) $12 \leq (SA_t) \leq \dfrac{54 \text{ m}^2}{100 \text{ gm fabric}}$ Examples 1, 2, 4 and 8 set forth below corresponded to the third grouping of fabrics.

As can be seen from the "Examples" shown on the following Table 1, materials suitable for the surge management portion can be produced from any of a number of nonwoven forming technologies. Each formation method can yield materials having different values for each of the distinguishing parameters previously defined. The examples show that the fabrics which can

EXAMPLE 1

Example 1 was a bonded carded web comprising 50 percent polyester fibers of 40 denier, 35 percent bleached cotton fibers of 1.5 denier and 15 percent Chisso ES fibers of 1.5 denier available from Chisso Corporation, Japan. The web had a basis of 211 gsm, a density of 0.034 g/cc and had been treated with a solution of Triton ® X102 surfactant (available from Rhom & Haas Co., Philadelphia, Pa.) by a dip and squeeze method to obtain a 0.5% surfactant add-on. Webs of this type can be produced by standard, carded web processes and equipment of the type available from J. D. Hollingsworth-on-Wheels Co. of Greenville, S.C.

EXAMPLE 2

A macro-fiber meltblown web was made having a 100 percent composition of a nylon-based polymer, sold as Hydrofil® nylon by Allied Fibers Corporation of Morristown, N.J. By the term "macro-fiber meltblown", it is meant that the web comprised fibers having a mean fiber size of about 23.1 microns (micrometers) and a fiber diameter size distribution of about 3.16 to 100 microns. The web had a basis weight of 213 grams per meter$^2$ and a density of 0.070 grams per centimeter$^3$.

EXAMPLE 3

A macro-fiber web was made similar to that Example 2, except that it had a basis weight of 216 grams per meter$^2$, a density of 0.111 grams per centimeter$^3$, a mean fiber diameter size of about 23.4 microns and a fiber diameter distribution of 2–159 microns.

EXAMPLE 4

A web was made of a pulp coform material, The web comprised a blend of 50 percent cellulosic fluff available as IP Supersoft from International Paper Corporation, and 50 percent macrofiber meltblown fibers of polypropylene, using resin available in pellet form from Himont U.S.A., Inc. of Wilmington, Del. The web was spray treated during formation with a solution of Triton X102 to obtain a 0.5% surfactant add-on. The meltblown polypropylene was believed to have fiber sizes ranging from about 10–113 microns and an average fiber size of about 50.2 microns. The web had a basis weight of 194 grams per meter$^2$, a density of 0.037 grams per centimeter$^3$ and was formed in accordance with the process described in U.S. Pat. No. 4,100,324 to Anderson and Sokolowski.

EXAMPLE 5

A bonded carded web was formed comprising about 40 wt % of 40 denier polyester fiber, about 25% of 3 denier rayon fiber, about 15% of 6.5 denier polyester fiber and about 20% of 6 denier Chisso ES fiber. The web had a basis weight of 223 gsm and a density of 0.045 gm/cc.

EXAMPLE 6

A staple coformed web of staple and melt extruded fibers was made according to the method described in the aforementioned U.S. Pat. No. 4,100,324 to Anderson and Sokolowski. The web comprised 50 percent meltblown microfibers of Hydrofil® nylon, and was believed to have an average fiber diameter of 14 microns with a range of from 2 microns to 80 microns, 38 percent polyester staple fibers of 25 denier and 12 percent Chisso ES fibers of 1.5 denier available from Chisso Corporation, Japan. The web had a basis weight of 203 grams per meter$^2$ and a density of 0.038 grams per centimeter$^3$.

EXAMPLE 7

A staple coformed web of staple and melt extruded fibers was made comprising 30 percent meltblown microfibers of polypropylene having a mean fiber diameter of 4 microns with a range of from 0.3 to 25 microns. Blended with the microfibers was: 56 percent polyester staple fibers of 25 denier, available from E. I. Dupont de Nemours Corporation of Wilmington Del.; and 14 percent Chisso ES fibers of 1.5 denier, available from Chisso Corporation, located in Japan. The web had a basis weight of 183 grams per meter$^2$, a density of 0.041 grams per centimeter$^3$ and was formed according to the process described in Example 6.

EXAMPLE 8

A staple coformed web was made according to the method described in Example 6, comprising 30 percent meltblown polypropylene microfibers having an average fiber diameter of 4 microns with a range of from 0.3 microns to 25 microns, blended with 56 percent polyester staple fibers of 25 denier, available from E. I. Dupont de Nemours Corporation of Wilmington, Del.; and 14 percent Chisso ES of 1.5 denier as in Example 7. The staple coformed web has a basis weight of 194 grams per meter$^2$ and a density of 0.023 grams per centimeter$^3$.

EXAMPLE 9

A 100 percent rayon spunbonded web was used, of the type sold by Futamura Chemicals, of Japan, under the tradename Taiko TCF. The web had a basis weight of 26 grams per meter$^2$ and a density of 0.112 grams per centimeter$^3$.

EXAMPLE 10

A nonwoven web having a basis weight of 239 grams per square meter and a density of 0.098 grams per cubic centimeter was made using 100% polypropylene macrofibers having an average fiber diameter of 44 microns, the fiber diameter ranging from about 5 to 200 microns. Himont PF-015 polypropylene was extruded through a bank of four polymer extrusion nozzles, each of which had a polymer orifice diameter of one millimeter. The polypropylene was heated to a temperature of 441° F. (208° C.) and pumped through the nozzle orifices at a throughput of 1.52 pounds per hole per hour (11.5 grams per hole per minute). To attenuate and draw the polymer exiting the polymer orifices into fibers, primary fiberization air was used to completely surround and contact the polymer streams emanating from each of the orifices. The primary fiberization air was supplied in completely surrounding contact by means of annular orifices positioned concentrically about each of the polymer orifices. Each of the annular orifices had a diameter of 5 millimeters. The air from the annular orifices was angled toward the streams of molten polymer at an angle of 7 degrees, the angle being measured as the interior angle between the intersection of the axis of the flow of polymer and a line tangent to the flow of the primary fiberization air. The polymer orifices contained within the nozzles were recessed two millimeters above the annular orifices used to emit the primary fiberization air.

To further fiberize the molten polymer stream, secondary fiberization air was also used. The secondary fiberization air comprised two fluid streams emanating from two, 2-millimeter diameter holes positioned exteriorly of the annular primary fiberization air orifice at a 180 degree separation. The fiberization air had an air flow rate of 23 scfm (0.0109 standard cubic meters per second) per nozzle with an air temperature of 455° F. (255° C.). The fibers thus created were collected in the form of a nonwoven web on a forming surface spaced approximately 15 to 20 inches (38–51 centimeters) from the nozzles and traveling at a speed of approximately 9 feet per minute (approximately 2.74 meters per minute).

EXAMPLE 11

A nonwoven web having a basis weight of 143 grams per square meter and a density of 0.124 grams per cubic centimeter was made using 100% Hydrofil® nylon microfibers having an average fiber diameter of 3 microns with a diameter range from about 0.3 to 25 microns. Allied Hydrofil® Nylon 6 (average molecular weight 20,000) was extruded through a bank of eight polymer extrusion nozzles each of which has a polymer orifice diameter of one millimeter. The polymer was heated to a temperature of 548 degrees F. (258 degrees C.) and pumped through the nozzle orifices at a throughput of 0.75 pounds per hole per hour (5.75 grams per hole per minute). To attenuate and draw the polymer exiting the polymer orifices into fibers, primary fiberization air was used to completely surround and contact the polymer streams emanating from each of the orifices. The primary fiberization air was supplied in completely surrounding contact by means of annular orifices positioned concentrically about each of the polymer orifices. Each of the annular orifices had a diameter of four millimeters. The air from the annular orifices was angled toward the streams of molten polymer at an angle of 45 degrees, the angle being measured as the interior angle between the intersection of the axis of the flow of polymer and a line tangent to the flow of the primary fiberization air. The polymer orifices contained within the nozzles were recessed two millimeters above the annular orificies used to emit the primary fiberization air.

To further fiberize the molten polymer stream, secondary fiberization air was also used. The secondary fiberization air comprised six fluid steams emanating from 1.5 millimeter diameter holes positioned exteriorly of the annular primary fiberization air orifice in groups of three at a 180 degree separation. The fiberization air had an air flow rate of 105 scfm (0.050 standard cubic meters per second) per nozzle with an air temperature of 679° F. (359° C.). The fibers thus created were collected in the form of a nonwoven web on a forming surface spaced approximately 15 to 20 inches (38–51 centimeters) from the nozzles and traveling at a speed of 5.5 feet per minute (1.68 meters per minute).

EXAMPLE 12

A pulp coform web was made using 30 percent cellulosic fluff fibers of IP Supersoft, coformed with 70 percent polypropylene meltblown microfibers and was believed to have an average fiber diameter of about 3.5 microns with a range of from 0.4 microns to 35 microns. The web had a basis weight of 108 grams per meter$^2$ and a density of 0.053 grams per centimeter$^3$.

EXAMPLE 13

A fibrous web composed of 100% woodpulp fluff and no superabsorbent polymer was constructed with a basis weight of 529 gsm and a density of 0.101 gm/cc.

It should be mentioned that, with respect to Examples 10 and 11, the melt-sprayed process is particularly adaptable to making unequally-formed, integrated structures wherein the various components, for example the surge management portion 46 and the retention portion 48, contain fibers which are intimately entangled or interwoven together at the fabric interfaces between the portions 46 and 48. This arrangement at the interfaces, improves capillarity between the functional portions.

With respect to Examples 7 and 8, it can be seen that resiliency can be imparted to the surge management portion by using a mixture of fibers having differing fiber diameters, the larger, stiffer fibers giving added void volume between the smaller high surface area fibers.

Having thus described the invention in rather full detail, it will be readily apparent that various changes and modifications may be made without departing from the spirit of the invention. All of such changes and modifications are contemplated as being within the scope of the present invention, as defined by the subjoined claims.

We claim:

1. An absorbent article, comprising:
   retention means for holding liquid;
   a fibrous surge management means located in liquid communication with said retention means for receiving said liquid and releasing said liquid to said retention means, said surge management means having a basis weight of at least about 60 gm/m$^2$, an uptake time value of not more than about 12 seconds and a liquid residual value of not more than about one gram per gram of said surge management means, and wherein said surge management means is constructed and arranged to provide said uptake time value and said liquid residual value over at least three uptake and desorption cycles.

2. An absorbent article as recited in claim 1, wherein said surge management means is constructed to further provide a temporary loading value of at least about 3 gm per gram of said surge management means over at least three uptake and desorption cycles.

3. An absorbent article as recited in claim 1, wherein said surge management means has a basis weight of within the range of about 90–3000 gsm.

4. An absorbent article as recited in claim 1, wherein said surge management means is constructed to provide an uptake time of not more than about 10 sec.

5. An absorbent article as recited in claim 1, wherein said surge management means is constructed to provide a temporary loading value of at least about 6 gm per gram of said surge management means.

6. An absorbent article as recited in claim 1, wherein said surge management means is constructed to provide a residual value of not more than about 0.75 gm per gram of said surge management means.

7. An absorbent article as recited in claim 1, wherein said surge management means is constructed to provide an uptake time of not more than about 8 sec.

8. An absorbent article as recited in claim 1, wherein said surge management means is constructed to provide a temporary loading value of at least about 9 gm per gram of said surge management means.

9. An absorbent article as recited in claim 1, wherein said surge management means is constructed to provide a residual value of not more than about 0.5 gm per gram of said surge management means.

10. An article as recited in claim 1, wherein said surge management means provides a wettable fiber-surface-area value of greater than zero and less than about 70 m$^2$ per 100 gm of said surge management means.

11. An absorbent article as recited in claim 10, wherein said surge management means is constructed to provide a wettable fiber-surface-area value (per 100 gm of said surge management means) which is not more than about 54 m$^2$.

12. An absorbent article as recited in claim 1, wherein said surge management means is constructed to provide a wettable-surface-area-times-density value of greater than zero and not more than about 7 m$^2$/100 cm$^3$.

13. An absorbent article as recited in claim 1, wherein said surge management means is constructed to provide a wettable-surface-area-times-density value which is greater than zero and not more than about 5 m$^2$/100 cm$^3$.

14. An article as recited in claim 1, wherein said surge management means is constructed to provide a total fiber-surface-area value which is within the range of about 5–90 m$^2$/100 gm of said surge management means.

15. An article as recited in claim 1, wherein said surge management means is constructed to provide a nonwettable-surface-area-times-density value which is not more than about 1.1 m$^2$/100 cm$^3$.

16. An article as recited in claim 1, wherein said surge management means is constructed to provide a nonwettable-surface-area-times-density value of not more than about 0.71 m$^2$/100 cm$^3$.

17. An article as recited in claim 1, wherein said surge management means is constructed to provide a wettable fiber-surface-area value within the range of about 3–54 m$^2$ per 100 gm of the surge management means.

18. An article as recited in claim 1, wherein said surge management means has a total fiber-surface-area value of not less than about 12 m$^2$ per 100 gm of said surge management means.

19. An article as recited in claim 3, wherein said surge management means has a total fiber-surface-area value of not less than about 5 m$^2$ per 100 gm of said surge management means.

20. An article as recited in claim 14, wherein said surge management means has a total fiber-surface-area value of not less than about 12 m$^2$ per 100 gm of said surge management means.

21. An absorbent article, comprising:
retention means for holding liquid;
a fibrous surge management means located in liquid communication with said retention means for receiving said liquid and releasing said liquid to said retention means, said surge management means having a basis weight of at least about 100 gm/m$^2$, an uptake time of not more than about 10 seconds and a liquid residual value of not more than about 0.75 gm per gram of said surge management means, and wherein said surge management means is constructed and arranged to provide said liquid uptake time and said liquid residual value over at least three uptake and desorption cycles.

22. An article as recited in claim 21, wherein said surge management means has a total fiber-surface-area value of not less than about 5 m$^2$ per 100 gm of said surge management means.

23. An absorbent article as recited in claim 21, wherein said surge management means is constructed to provide a temporary loading value of least about 3 gm per gram of said surge management means.

24. An absorbent article as recited in claim 21, wherein said surge management means is constructed to provide a temporary loading value of least about 6 gm per gram of said surge management means.

25. An absorbent article as recited in claim 21, wherein said surge management means is constructed to provide a temporary loading value of least about 6 gm per gram of said surge management means, and a liquid residual value of not more than about 0.5 gm per gram of said surge management means.

26. An absorbent article as recited in claim 21, wherein said surge management means is constructed to provide an uptake time of not more than about 8 sec.

27. An absorbent article as recited in claim 21, wherein said surge management means is constructed to provide a temporary loading value of at least about 9 gm per gram of said surge management means.

28. An absorbent article as recited in claim 21, wherein said surge management means is constructed to provide a residual value of not more than about 0.5 gm per gram of said surge management means.

29. An article as recited in claim 21, wherein said surge management means provides a wettable fiber-surface-area value of greater than zero and less than about 70 m$^2$ per 100 gm of said surge management means.

30. An absorbent article as recited in claim 21, wherein said surge management means is constructed to provide a wettable fiber-surface-area value (per 100 gm of said surge management means) which is not more than about 54 m$^2$.

31. An absorbent article as recited in claim 21, wherein said surge management means is constructed to provide a wettable-surface-area-times-density value of greater than zero and not more than about 7 m$^2$/100 cm$^3$.

32. An absorbent article as recited in claim 21, wherein said surge management means is constructed to provide a wettable-surface-area-times-density value which is greater than zero and not more than about 4 m$^2$/100 cm$^3$.

33. An article as recited in claim 21, wherein said surge management means is constructed to provide a nonwettable-surface-area-times-density value of not more than about 1.1 m$^2$/100 cm$^3$.

34. An article as recited in claim 21, wherein said surge management means is constructed to provide a nonwettable-surface-area-times-density value which is not more than 0.71 m$^2$/100 cm$^3$.

35. An absorbent article, comprising:
retention means for holding liquid;
a fibrous surge management means located in liquid communication with said retention means for receiving said liquid and releasing said liquid to said retention means, said surge management means having a basis weight of at least about 100 gm/m$^2$, an uptake time of not more than about 8 seconds and a liquid residual value of not more than about 0.5 gm per gram of said management means, and wherein said surge management means is constructed and arranged to provide said uptake time and said liquid residual value over at least three uptake and desorption cycles.

36. An article as recited in claim 35, wherein said surge management means has a total fiber-surface-area value of not less than about 5 m$^2$ per 100 gm of said surge management means.

37. An absorbent article as recited in claim 35, wherein said surge management means is constructed to provide a temporary loading value of at least about 3 gm per gram of said surge management means.

38. An absorbent article as recited in claim 35, wherein said surge management means is constructed to provide a temporary loading value of at least about 6 gm per gram of said surge management means.

39. An absorbent article as recited in claim 35, wherein said surge management means is constructed to provide a temporary loading value of at least about 9 gm per gram of said surge management means.

40. An article as recited in claim 35, wherein said surge management means provides a wettable fiber-surface-area value of greater than zero and less than about 70 m$^2$ per 100 gm of said surge management means.

41. An absorbent article as recited in claim 35, wherein said surge management means is constructed to provide a wettable fiber-surface-area value (per 100 gm of said surge management means) which is not more than about 54 m$^2$.

42. An absorbent article as recited in claim 35, wherein said surge management means is constructed to provide a wettable-surface-area-times-density value (per 100 cm$^3$ of said surge management means) of greater than zero and not more than about 7 m$^2$.

43. An absorbent article as recited in claim 35, wherein said surge management means is constructed to provide a wettable-surface-area-times-density value which is not more than about 4 m$^2$/100 cm$^3$ of surge management means.

44. An article as recited in claim 35, wherein said surge management means is constructed to provide a nonwettable-surface-area-times-density value of not more than about 1.1 m$^2$/100 cm$^3$ of surge management means.

45. An article as recited in claim 35, wherein said surge management means is constructed to provide a nonwettable-surface-area-times-density value which is not more than about 0.71 m$^2$/100 cm$^3$ of surge management means.

46. An absorbent article, comprising:
retention means for holding a liquid;
a fibrous surge management means located in liquid communication with said retention means for receiving said liquid and releasing said liquid to said retention means, said surge management means having a basis weight of at least about 60 gm/m$^2$, an uptake time value of not more than about 12 seconds, a temporary loading value of at least about 3 gm per gram of said surge management means, and a liquid residual value of not more than about one gram per gram of said surge management means, wherein said surge management means is constructed and arranged to provide said uptake time value, said temporary loading value and said liquid residual value over at least three uptake and desorption cycles, and said surge management means further having a wettable fiber-surface-area value of not more than about 70 m$^2$ per 100 gm of said surge management means, a wettable-fiber-surface-area-times-density value of greater than zero and not more than about 7 m$^2$/100 cm$^3$, a nonwettable-fiber-surface-area-times-density value of not more than about 1.1 m$^2$/100 cm$^3$ of said surge management means, and a total fiber-surface-area value within the range of about 5–90 m$^2$ per 100 gm of said surge management means.

47. An article as recited in claim 46, wherein said surge management means has a total fiber-surface-area value of not less than about 12 m$^2$ per 100 gm of said surge management means.

48. An absorbent article as recited in claim 46, wherein said surge management means has a wettable fiber-surface-area value within the range of about 3–54 m$^2$/100 gm of said surge management means, a wettable-fiber-surface-area-times-density value greater than zero and not more than about 5 m$^2$/100 cm$^3$ of said surge management means, a nonwettable-fiber-surface-area-times-density value of not more than about 1.1 m$^2$/100 cm$^3$ of said surge management means, and a total fiber-surface-area value within the range of about 5–54 m$^2$/100 gm of said surge management means.

49. An article as recited in claim 48, wherein said surge management means has a total fiber-surface-area value of not less than about 12 m$^2$ per 100 gm of said surge management means.

50. An absorbent article as recited in claim 46, wherein said surge management means has a wettable fiber-surface-area value within the range of about 3–54 m$^2$/100 gm of said surge management means, a wettable-fiber-surface-area-times-density value greater than zero and not more than about 4 m$^2$/100 cm$^3$ of said surge management means, a nonwettable-fiber-surface-area-times-density value of not more than about 0.71 m$^2$/100 cm$^3$ of said surge management means, and a total fiber-surface-area value within the range of about 12–54 m$^2$/100 gm of said surge management means.

51. An absorbent article, comprising:
retention means for holding a liquid;
a fibrous surge management means located in liquid communication with said retention means for receiving said liquid and releasing said liquid to said retention means, said surge management means having a basis weight of at least about 60 gm/m$^2$, an uptake time value of not more than about 10 seconds, a temporary loading value of at least about 6 gm per gram of said surge management means, and a liquid residual value of not more than about 0.75 gm per gram of said surge management means, wherein said surge management means is constructed and arranged to provide said uptake time value, said temporary loading value and said liquid residual value over at least three uptake and desorption cycles, and said surge management means further having a wettable fiber-surface-area value within the range of about 3–54 m$^2$ per 100 gm of said surge management means, a wettable-fiber-surface-area-times-density value of greater than zero and not more than about 5 m$^2$/100 cm$^3$, a nonwettable-fiber-surface-area-times-density value of not more than about 1.1 m$^2$/100 cm$^3$ of said surge management means, and a total fiber surface area value within the range of about 5–54 m$^2$ per 100 gm of said surge management means.

52. An article as recited in claim 51, wherein said surge management means has a total fiber-surface-area value of not less than about 12 m$^2$ per 100 gm of said surge management means.

53. An absorbent article as recited in claim 51, wherein said surge management means has a wettable fiber-surface-area value within the range of about 3–54 m$^2$/100 gm of said surge management means, a wettable-fiber-surface-area-times-density value greater than zero and not more than about 4 m$^2$/100 cm$^3$ of said surge management means, a nonwettable-fiber-surface-area-times-density value of not more than about 0.71 m$^2$/100 cm$^3$ of said surge management means, and a total fiber-surface-area value within the range of about 12–54 m$^2$/100 gm of said surge management means.

54. An absorbent article, comprising:
retention means for holding a liquid;
a fibrous surge management means located in liquid communication with said retention means for receiving said liquid and releasing said liquid to said retention means, said surge management means having a basis weight of at least about 60 gm/m², an uptake time value of not more than about 8 seconds, a temporary loading value of at least about 9 gm per gram of said surge management means, and a liquid residual value of not more than about 0.5 gm per gram of said surge management means, wherein said surge management means is constructed and arranged to provide said uptake time value, said temporary loading value and said liquid residual value over at least three uptake and desorption cycles, and said surge management means further having a wettable fiber-surface-area value within the range of about 3–54 m² per 100 gm of said surge management means, a wettable-fiber-surface-area-times-density value of greater than zero and not more than about 4 m²/100 cm³, a nonwettable-fiber-surface-area-times-density value of not more than about 0.71 m²/100 cm³ of said surge management means, and a total fiber surface area value within the range of about 12–54 m² per 100 gm of said surge management means.

55. An absorbent article as recited in claim 54, wherein said surge management means has a basis weight of at least about 100 gm/m².

56. An absorbent article, comprising:
retention means for holding a liquid;
a fibrous surge management means located in liquid communication with said retention means for receiving said liquid and releasing said liquid to said retention means, said surge management means having a basis weight of at least about 100 gm/m², an uptake time value of not more than about 12 seconds, a temporary loading value of at least about 3 gm per gram of said surge management means, and a liquid residual value of not more than about one gram per gram of said surge management means, wherein said surge management means is constructed and arranged to provide said uptake time value, said temporary loading value and said liquid residual value over at least three uptake and desorption cycles, and said surge management means further having a wettable fiber-surface-area value of not more than about 70 m² per 100 gm of said surge management means, a wettable-fiber-surface-area-times-density value of greater than zero and not more than about 7 m²/100 cm³, a nonwettable-fiber-surface-area-times-density value of not more than about 1.1 m²/100 cm³ of said surge management means, and a total fiber surface area value within the range of about 5–90 m² per 100 gm of said surge management means.

57. An absorbent article as recited in claim 56, wherein said surge management means has a wettable fiber-surface-area value within the range of about 3–54 m²/100 gm of said surge management means, a wettable-fiber-surface-area-times-density value greater than zero and not more than about 5 m²/100 cm³ of said surge management means, a nonwettable-fiber-surface-area-times-density value of not more than about 1.1 m²/100 cm³ of said surge management means, and a total fiber-surface-area value within the range of about 5–54 m²/100 gm of said surge management means.

58. An absorbent article as recited in claim 56, wherein said surge management means has a wettable fiber-surface-area value within the range of about 3–54 m²/100 gm of said surge management means, a wettable-fiber-surface-area-times-density value greater than zero and not more than about 4 m²/100 cm³ of said surge management means, a nonwettable-fiber-surface-area-times-density value of not more than about 0.71 m²/100 cm³ of said surge management means, and a total fiber-surface-area value within the range of about 12–54 m²/100 gm of said surge management means.

59. An absorbent article, comprising:
retention means for holding a liquid;
a fibrous surge management means located in liquid communication with said retention means for receiving said liquid and releasing said liquid to said retention means, said surge management means having a basis weight of at least about 100 gm/m², an uptake time value of not more than about 10 seconds, a temporary loading value of at least about 6 gm per gram of said surge management means, and a liquid residual value of not more than about 0.75 gm per gram of said surge management means, wherein said surge management means is constructed and arranged to provide said uptake time value, said temporary loading value and said liquid residual value over at least three uptake and desorption cycles, and said surge management means further having a wettable fiber-surface-area value within the range of about 3–54 m² per 100 gm of said surge management means, a wettable-fiber-surface-area-times-density value of greater than zero and not more than about 5 m²/100 cm³, a nonwettable-fiber-surface-area-times-density value of not more than about 1.1 m²/100 cm³ of said surge management means, and a total fiber surface area value within the range of about 5–54 m² per 100 gm of said surge management means.

60. An absorbent article as recited in claim 59, wherein said surge management means has a wettable fiber-surface-area value within the range of about 3–54 m²/100 gm of said surge management means, a wettable-fiber-surface-area-times-density value greater than zero and not more than about 4 m²/100 cm³ of said surge management means, a nonwettable-fiber-surface-area-times-density value of not more than about 0.71 m²/100 cm³ of said surge management means, and a total fiber-surface-area value within the range of about 12–54 m²/100 gm of said surge management means.

61. An absorbent article, comprising:
retention means for holding a liquid;
a fibrous surge management means located in liquid communication with said retention means for receiving said liquid and releasing said liquid to said retention means, said surge management means having a basis weight of at least about 60 gm/m², a wettable fiber-surface-area value of not more than about 70 m² per 100 gm of said surge management means, a wettable-fiber-surface-area-times-density value of greater than zero and not more than about 7 m²/100 cm³, a nonwettable-fiber-surface-area-times-density value of not more than about 1.1 m²/100 cm³ of said surge management means, and a total fiber surface area value within the range of about 5–90 m² per 100 gm of said surge management means.

62. An article as recited in claim 61, wherein said surge management means has a total fiber-surface-area value of not less than about 12 m² per 100 gm of said surge management means.

63. An absorbent article as recited in claim 61, wherein said surge management means has an uptake time value of not more than about 10 seconds, a temporary loading value of at least about 6 gm per gram of said surge management means, and a liquid residual value of not more than about 0.75 gm per gram of said surge management means, wherein said surge management means is constructed and arranged to provide said uptake time value, said temporary loading value and said liquid residual value over at least three uptake and desorption cycles.

64. An absorbent article as recited in claim 63, wherein said surge management means has an uptake time value of not more than about 8 seconds, a temporary loading value of at least about 9 gm per gram of said surge management means, and a liquid residual value of not more than about 0.5 gm per gram of said surge management means.

65. An absorbent article as recited in claim 61, wherein said surge management means has a wettable fiber-surface-area value within the range of about 3–54 $m^2/100$ gm of said surge management means, a wettable-fiber-surface-area-times-density value greater than zero and not more than about 5 $m^2/100$ $cm^3$ of said surge management means, a nonwettable-fiber-surface-area-times-density value of not more than about 1.1 $m^2/100$ $cm^3$ of said surge management means, and a total fiber-surface-area value within the range of about 5–54 $m^2/100$ gm of said surge management means.

66. An article as recited in claim 65, wherein said surge management means has a total fiber-surface-area value of not less than about 12 $m^2$ per 100 gm of said surge management means.

67. An article as recited in claim 61, wherein said surge management means has a basis weight of at least about 100 $gm/m^2$.

68. An absorbent article as recited in claim 65, wherein said surge management means has an uptake time value of not more than about 8 seconds, a temporary loading value of at least about 9 gm per gram of said surge management means, and a liquid residual value of not more than about 0.5 gm per gram of said surge management means, wherein said surge management means is constructed and arranged to provide said uptake time value, said temporary loading value and said liquid residual value over at least three uptake and desorption cycles.

69. An absorbent article as recited in claim 61, wherein said surge management means has a wettable fiber-surface-area value within the range of about 3–54 $m^2/100$ gm of said surge management means, a wettable-fiber-surface-area-times-density value greater than zero and not more than about 4 $m^2/100$ $cm^3$ of said surge management means, a nonwettable-fiber-surface-area-times-density value of not more than about 0.71 $m^2/100$ $cm^3$ of said surge management means, and a total fiber-surface-area value within the range of about 12–54 $m^2/100$ gm of said surge management means.

70. An absorbent article as recited in claim 61, wherein said surge management means has a basis weight of at least about 100 $gm/m^2$.

71. An absorbent article as recited in claim 70, wherein said surge management means has an uptake time value of not more than about 10 seconds, a temporary loading value of at least about 6 gm per gram of said surge management means, and a liquid residual value of not more than about 0.75 gm per gram of said surge management means, wherein said surge management means is constructed and arranged to provide said uptake time value, said temporary loading value and said liquid residual value over at least three uptake and desorption cycles.

72. An absorbent article as recited in claim 71, wherein said surge management means has an uptake time value of not more than about 8 seconds, a temporary loading value of at least about 9 gm per gram of said surge management means, and a liquid residual value of not more than about 0.5 gm per gram of said surge management means.

73. An absorbent article as recited in claim 61, wherein said surge management means has a basis weight of at least about 100 $gm/m^2$, a wettable fiber-surface-area value within the range of about 3–54 $m^2/100$ gm of said surge management means, a wettable-fiber-surface-area-times-density value greater than zero and not more than about 5 $m^2/100$ $cm^3$ of said surge management means, a nonwettable-fiber-surface-area-times-density value of not more than about 1.1 $m^2/100$ $cm^3$ of said surge management means, and a total fiber-surface-area value within the range of about 5–54 $m^2/100$ gm of said surge management means.

74. An absorbent article as recited in claim 73, wherein said surge management means has an uptake time value of not more than about 8 seconds, a temporary loading value of at least about 9 gm per gram of said surge management means, and a liquid residual value of not more than about 0.5 gm per gram of said surge management means, wherein said surge management means is constructed and arranged to provide said uptake time value, said temporary loading value and said liquid residual value over at least three uptake and desorption cycles.

75. An absorbent article as recited in claim 61, wherein said surge management means has a basis weight of at least about 100 $gm/m^2$, a wettable fiber-surface-area value within the range of about 3–54 $m^2/100$ gm of said surge management means, a wettable-fiber-surface-area-times-density value greater than zero and not more than about 4 $m^2/100$ $cm^3$ of said surge management means, a nonwettable-fiber-surface-area-times-density value of not more than about 0.71 $m^2/100$ $cm^3$ of said surge management means, and a total fiber-surface-area value within the range of about 12–54 $m^2/100$ gm of said surge management means.

76. An absorbent article, comprising:
retention means for holding liquid;
a fibrous surge management means located in liquid communication with said retention means for receiving said liquid and releasing said liquid to said retention means, said surge management means having a basis weight of at least about 60 $gm/m^2$, a total fiber-surface-area value which is not less than about 12 $m^2$ per 100 gm of said surge management means, an uptake time value of not more than about 12 seconds, a liquid residual value of not more than about one gram per gram of said surge management means and a temporary loading value of at least about 3 gm per gram of said surge management means, wherein said surge management means is constructed and arranged to provide said uptake time value, said liquid residual value and said temporary loading value over at least three uptake and desorption cycles.

77. An absorbent article as recited in claim 76 wherein said fibrous surge management means has a basis weight of at least about 90 $gm/m^2$.

78. An absorbent article as recited in claim 76 wherein said fibrous surge management means has a total fiber-surface-area value of not more than about 54 m² per 100 gm of said surge management means.

79. An absorbent article as recited in claim 78 wherein said fibrous surge management means has a basis weight of at least about 90 gm/m².

80. An absorbent article, comprising:

retention means for holding liquid;

a fibrous surge management means located in liquid communication with said retention means for receiving said liquid and releasing said liquid to said retention means, said surge management means having a basis weight of at least about 90 gm/m², a total fiber-surface-area value within the range of about 5–90 m² per 100 gm of said surge management means, an uptake value of not more than about 12 seconds, a liquid residual value of not more than about one gram per gram of said surge management means and a temporary loading value of at least about 3 gm per gram of said surge management means, wherein said surge management means is constructed and arranged to provide said uptake time value, said liquid residual value and said temporary loading value over at least three uptake and desorption cycles.

81. An absorbent article as recited in claim 80 wherein said fibrous surge management means has a total fiber-surface-area value within the range of about 5–54 m² per 100 gm of said surge management means.

* * * * *